United States Patent
Chow et al.

(10) Patent No.: US 6,858,032 B2
(45) Date of Patent: Feb. 22, 2005

(54) ROTATING TRACK CUTTING GUIDE SYSTEM

(75) Inventors: Steven Chow, North Oaks, MN (US); Ramon B. Gustilo, Eden Prairie, MN (US); William D. Lew, Mendotah Heights, MN (US)

(73) Assignee: Midwest Orthopaedic Research Foundation, Minneapolis, MN (US)

( * ) Notice: Subject to any disclaimer, the term of this patent is extended or adjusted under 35 U.S.C. 154(b) by 96 days.

(21) Appl. No.: 10/121,461

(22) Filed: Apr. 12, 2002

(65) Prior Publication Data

US 2003/0045883 A1 Mar. 6, 2003

Related U.S. Application Data

(60) Provisional application No. 60/314,475, filed on Aug. 23, 2001.

(51) Int. Cl.[7] .................................................. A61B 17/58
(52) U.S. Cl. .............................. 606/80; 606/86; 606/88
(58) Field of Search ........................... 606/80, 88, 102, 606/86, 87, 89, 79, 96

(56) References Cited

U.S. PATENT DOCUMENTS

| | | | | |
|---|---|---|---|---|
| 4,457,307 A | * | 7/1984 | Stillwell | 606/88 |
| 4,574,794 A | * | 3/1986 | Cooke et al. | 606/88 |
| 5,007,912 A | | 4/1991 | Albrektsson | |
| 5,042,983 A | * | 8/1991 | Rayhack | 606/87 |
| 5,228,459 A | | 7/1993 | Caspari | |
| 5,304,181 A | | 4/1994 | Caspari | |
| 5,624,444 A | * | 4/1997 | Wixon et al. | 606/88 |
| 5,653,714 A | | 8/1997 | Dietz | |
| 5,681,320 A | * | 10/1997 | McGuire | 606/104 |
| 6,290,704 B1 | * | 9/2001 | Burkinshaw et al. | 606/88 |
| 6,468,280 B1 | * | 10/2002 | Saenger et al. | 606/88 |
| 6,551,324 B2 | * | 4/2003 | Muller | 606/88 |

* cited by examiner

*Primary Examiner*—Pedro Philogene
(74) *Attorney, Agent, or Firm*—Patterson, Thuente, Skaar & Christensen, P.A.

(57) ABSTRACT

The present invention is a rotating track cutting guide system that maintains precise alignment of a bone saw with bone tissue. The rotating track cutting guide generally includes a track subassembly and cutting guide subassemblies attachable to the bone that is to be cut. The track subassembly supports an oscillating surgical saw driver. The track subassembly is removably securable to cutting guide subassemblies which are attachable to the desired bone to facilitate a series of controlled cuts. The design of the track subassembly stabilizes the oscillating saw driver and enables it to both rotate in the plane of the saw blade and move linearly along the track.

56 Claims, 18 Drawing Sheets

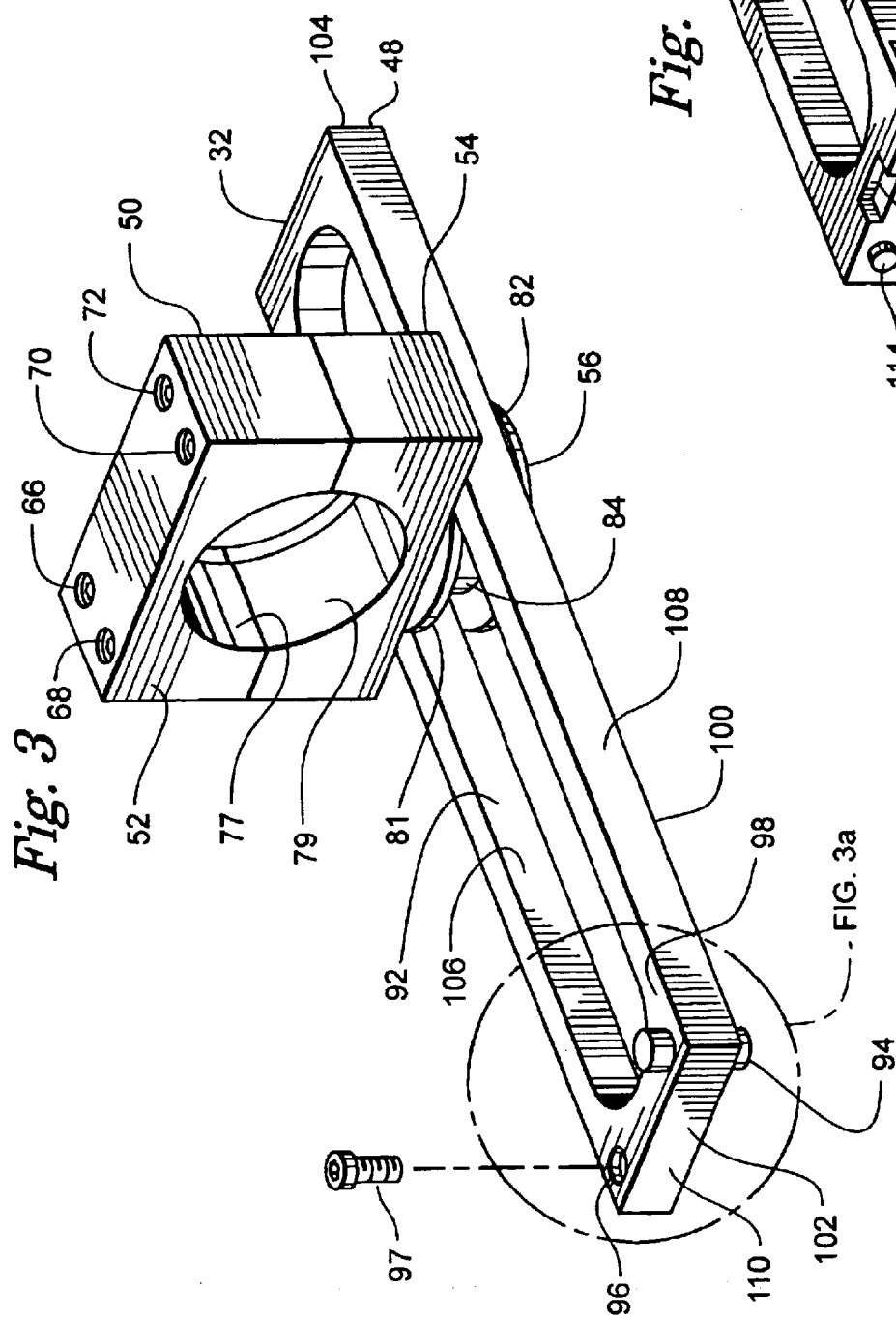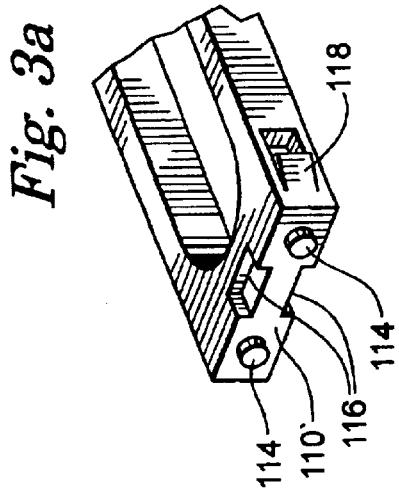

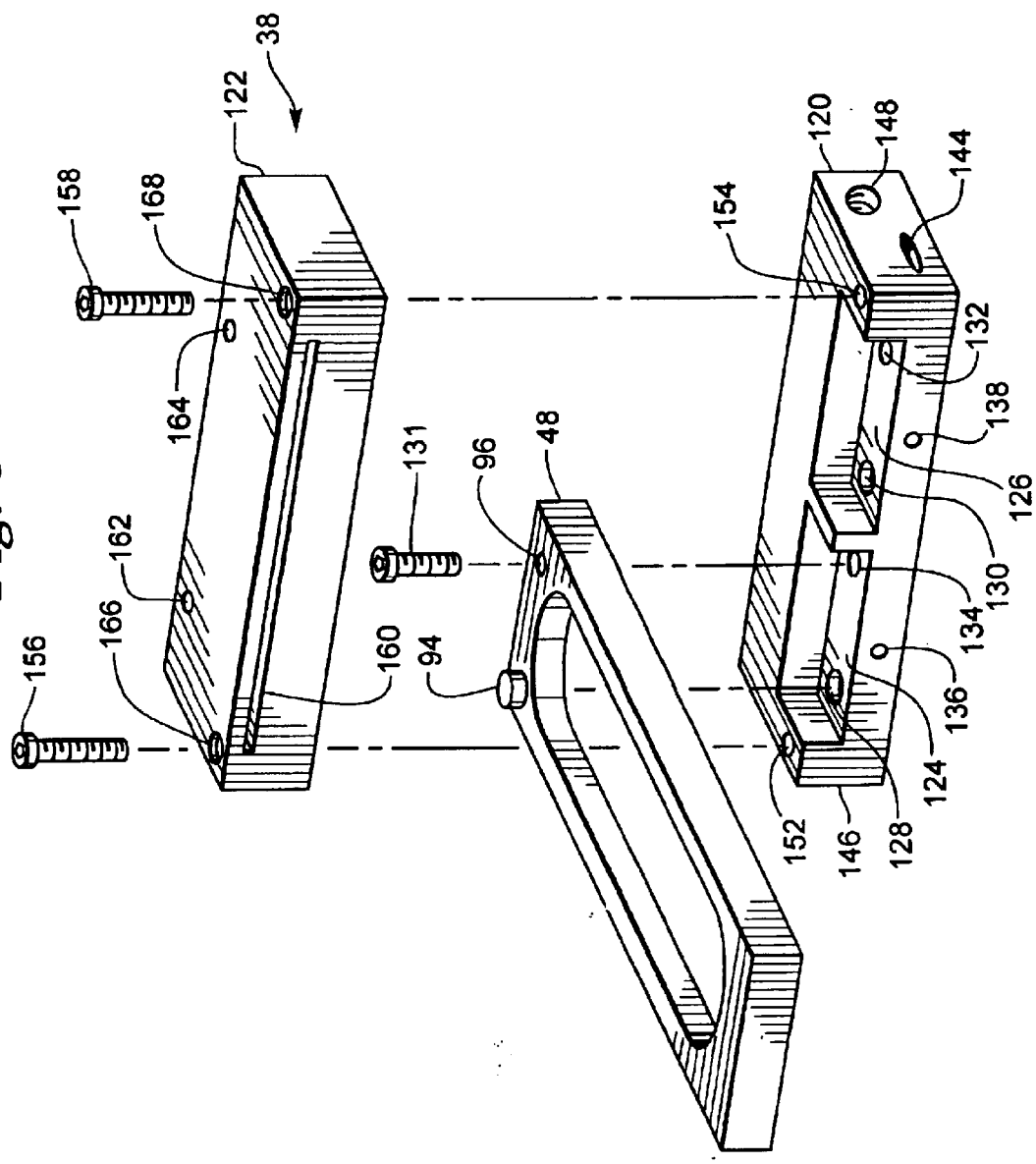

ROTATING TRACK CUTTING GUIDE SYSTEM

This application claims priority to U.S. Provisional Application No. 60/314,475 filed Aug. 23, 2001, the contents of which are incorporated herein in their entirety by this reference.

FIELD OF THE INVENTION

The present invention relates to instrumentation used for precision bone cutting. More specifically, the invention relates to a cutting guide apparatus for guiding a bone saw to allow for the surgical preparation of bone joint structures to facilitate the implantation of artificial joint prostheses.

BACKGROUND OF THE INVENTION

In total knee arthroplasty, a damaged knee joint is replaced with a prosthesis to reproduce natural knee function. Multiple faceted cuts are made on the femur and at least one cut is made to the tibia to prepare the bone surface for application of the knee replacement prosthesis. These cut surfaces are preferably precisely angularly aligned to each other and are planar to enable satisfactory mating with the prosthesis.

In preparing the joint for a prosthesis, a series of cuts are made to the inferior end of the femur and the superior end of the tibia. Exemplary femoral cuts are depicted in FIG. 1. Initially the femur is cut to create a flat surface (annotated "A" in the drawings) generally perpendicular to the longitudinal mechanical axis of the bone. Next, two flat cuts are made generally parallel to the longitudinal mechanical axis of the femur: one at the rear of the knee to remove the posterior femoral condyles B and another at the front of the knee C. Lastly, two chamfered cuts D, D' are made at approximately a forty-five degree angle at the juncture of the perpendicular and the anterior and posterior planes (or "planed femoral surfaces"). The superior end of the tibia is cut off perpendicular to the longitudinal mechanical axis of the tibia in a fashion similar to femoral cut A.

Skeletal joints are subject to high degrees of mechanical stress. The secure attachment of joint replacement structures to the bone is, therefore, critical in determining the long-term success of the surgical procedure. The accuracy with which the bone ends are shaped is essential to achieving a secure connection between the existing bone and an implanted prosthesis.

A number of studies have documented the correlation between imprecise bonding surface preparation and later complications for joint replacement patients. Knee implant malpositioning due to deficient bone resecting technique contributes to poor long-term results by influencing a prosthesis' function, load distribution, wear and fixation.

These discoveries have led researchers to propose standards that improve the likelihood of post-surgical success. Sandborn et al. recommended that the gap between the bone and a porous-coated knee implant not exceed 0.5 mm for optimal bone ingrowth. P. M. Sandborn et al., *The Effect Of Surgical Fit On Bone Growth Into Porous Coated Implants*, 12 Trans. Orthop. Res. Soc., 217 (1987). Cooke et al proposed a maximum cutting error of ±1 mm for proper bone fixation into a porous-coated prosthesis. T. D. Cooke et al., *Universal Bone Cutting Device For Precision Knee Replacement Arthroplasty And Osteotomy*. 7 J. Biomed. Eng. 45, 50 (1985). These levels of accuracy are currently difficult to achieve.

Unfortunately, these currently exists as much as a ten-fold discrepancy between the precision of the implant manufacturing tolerances (±0.2 mm) and the bone cutting process. Bone cements are often used to fill the gap between resected bone tissue and the prosthesis. Even with the use of bone cement, however, an uneven cement mantle due to poor bone cutting can result in early prosthesis loosening.

To aid the surgeon in making the precise multiple bone cuts required for this type of surgery, various guides and devices have been proposed. An initial group of devices are secured to the saw driver and to the patient and/or the surgical table. A second group includes cutting guides that guide the saw blade, typically within a close fitting slot.

The first group includes, for example, U.S. Pat. No. 4,457,307, issued to Stillwell, which discloses a bone cutting device for total knee replacements that is secured to the femur throughout its use. With this device, cuts are made both to the femur and the tibia. The Stillwell design requires removal of a large amount of soft tissue and a substantial number of calculations and adjustments in order to make the cuts required for total knee replacement surgery.

U.S. Pat. No. 4,574,794, issued to Cooke et al., discloses a guide for supporting a bone saw driver. The Cooke guide includes a complex system of parallel guide rods secured to the operating table as well as to the long bones of the leg and the bones of the foot. The device requires extensive fixation to the bone and numerous calculations to generate the desired cuts on the knee joint. U.S. Pat. No. 5,007,912, issued to Albrektsson et al., discloses a cutting device mounted to a frame. The frame is connected to the patient's femur and to the operating table. Similar to the Cooke device, this system requires extensive manipulation of the saw driver and the patient to create the required cuts.

U.S. Pat. No. 5,092,869, issued to Waldron, discloses a surgical saw guide, including retractable guide pins mounted in guide pin holders which stabilize the saw for translational movement along a linear axis.

U.S. Pat. Nos. 5,228,459 and 5,304,181, issued to Caspari et al., disclose an apparatus that is affixed to the tibia and the ankle that includes a rack and pinion mechanism to linearly advance a surgical milling device to make the appropriate surface cuts for total knee replacement surgery. The '181 patent discloses refinements to the device of the '459 patent.

U.S. Pat. No. 5,653,714, issued to Dietz et al., discloses a multi-component assembly that slides and pivots a milling head in order to make the cuts required for knee replacement surgery.

The second group of cutting guide systems includes devices such as that disclosed in U.S. Pat. No. 5,925,049, issued to Gustilo et al. The Gustilo patent discloses slotted cutting guides which are secured to the bone end by screws or other fixtures. Slotted cutting guides assist in orienting the blade of a surgical bone saw during the cutting process.

Despite these efforts, there remains room for improvement in the creation of precise and accurate bone cuts with current cutting technologies.

Devices that guide the saw body tend to be complex and cumbersome to set up, adjust and use. Orthopedic surgery is a physically demanding, labor intensive and time-consuming endeavor. Added instrument complexity tends to lead to longer procedures, which results in surgeon fatigue and a greater chance of surgical error.

Surgical cutting guides tend to obstruct the surgeon's view of the cutting site. This increases the risk of inadvertent damage to surrounding tissue, and can reduce the accuracy of a cut.

The oscillating saw used by orthopedic surgeons can be guided along a surgical cutting guide by hand. Some cutting guides utilize slots to provide a measure of blade control during surgery. There are numerous limitations with this cutting methodology. The very nature of resting an oscillating saw blade against another surface while the saw blade is in motion creates a certain degree of imprecision.

Also, to allow clearance for the saw in the kerf, surgical bone saw teeth are set. That is, alternate teeth are offset from the center of the blade so that the resulting cut is slightly wider than the blade, to prevent the blade binding in the kerf. Consequently, the guide slot must be wide enough to receive the set of the teeth. This creates enough clearance for the blade to toggle within the slot and substantially reduce the precision of the cut.

The surgeon's hand motions can cause the blade to toggle during the procedure and generate a non-planar bone surface. Vibrations generated by the oscillating saw driver are transmitted to the hands of the surgeon and to the cutting guide, affecting the quality of the resected bone surface.

In addition, inadvertent blade contact with the inner slot surface of a cutting guide dulls the blade teeth and damages the guide slot. Contact between the blade and guide can also result in a temporary loss of blade control. Consequently, it is difficult to maintain the saw oriented in the desired plane and angle.

Additionally, current cutting guide sets contain a large number of precision machined parts. These parts are expensive and their multiplicity creates both added expense and complexity. It would be preferable if the orthopedic surgeon had available a simpler cutting guide system with relatively few parts.

Thus, there is a need for a surgical saw guide that allows for the precise faceting of bone ends to facilitate the implantation of orthopedic prostheses. The guide should be simple to set up and use while creating precision planar cuts in bone tissue. It is preferred that the guide minimize saw blade damage and wear and that the guide minimize vibrational energy transfer to the surgeon's hands and the patient's bone. It would be preferable to minimize the amount of visual obstruction presented by the cutting guide.

SUMMARY OF THE INVENTION

The present invention fulfills the above needs by providing a rotating track cutting guide system that maintains precise alignment of a bone saw with bone tissue. The rotating track cutting guide system generally includes a track subassembly and cutting guide subassemblies attachable to the bone that is to be cut. The track subassembly supports an oscillating surgical saw driver. The track subassembly is removably securable to cutting guide subassemblies which are attachable to the desired bone to facilitate a series of controlled cuts. The design of the track subassembly stabilizes the oscillating saw driver and enables it to both rotate in the plane of the saw blade and move linearly along the track. In conjunction with specially designed cutting guide subassemblies, use of the track subassembly enables a surgeon using the rotating track cutting guide system to perform all the necessary surgical cuts required for a knee replacement with great accuracy and precision. The rotating track cutting guide system is adaptable to an open frame design to improve visibility of the surgical site during resection. Although the rotating track cutting guide system will be described in the context of total knee arthroplasties, it should be understood that the invention may be applied to various other surgical procedures.

The track subassembly includes a rotating driver carriage that supports an oscillating saw driver. The driver carriage rests upon a track that has an alignment member that enables the track to removably attach to various positioning and cutting guides. The alignment member allows immediate fixation of the track onto the cutting guide subassembly, while fastening members provide for ready attachment and removal. The use of a stabilizing track in conjunction with cutting and positioning guides results in a synergistic effect that enables the user to resect bone to great accuracy and precision along a plane.

The present invention provides a cutting platform whereby the oscillating saw driver, the cutting guide and the bone to be cut are fixed relative to one another except in the plane in which the cut is being made. The stabilization of movement affords the surgeon excellent control and enables the physician to perform precise and accurate cuts.

Further, the rotating track cutting guide system minimizes blade damage and wear caused by inadvertent contact between the blade and the cutting guide. The resulting retention of blade sharpness throughout the procedure produces a smoother, flatter, more precisely cut bone surface than is otherwise achievable.

BRIEF DESCRIPTION OF THE DRAWINGS

FIG. 3 is a top perspective view of a track subassembly in accordance with the present invention;

FIG. 3a is a detail view of a second embodiment of the end of the track subassembly (taken at the position of 3a of FIG. 3);

FIG. 6 is an exploded front perspective view of the distal femur and proximal tibia cutting guide subassembly and track in accordance with the present invention;

DETAILED DESCRIPTION OF THE INVENTION

Figure 1A:
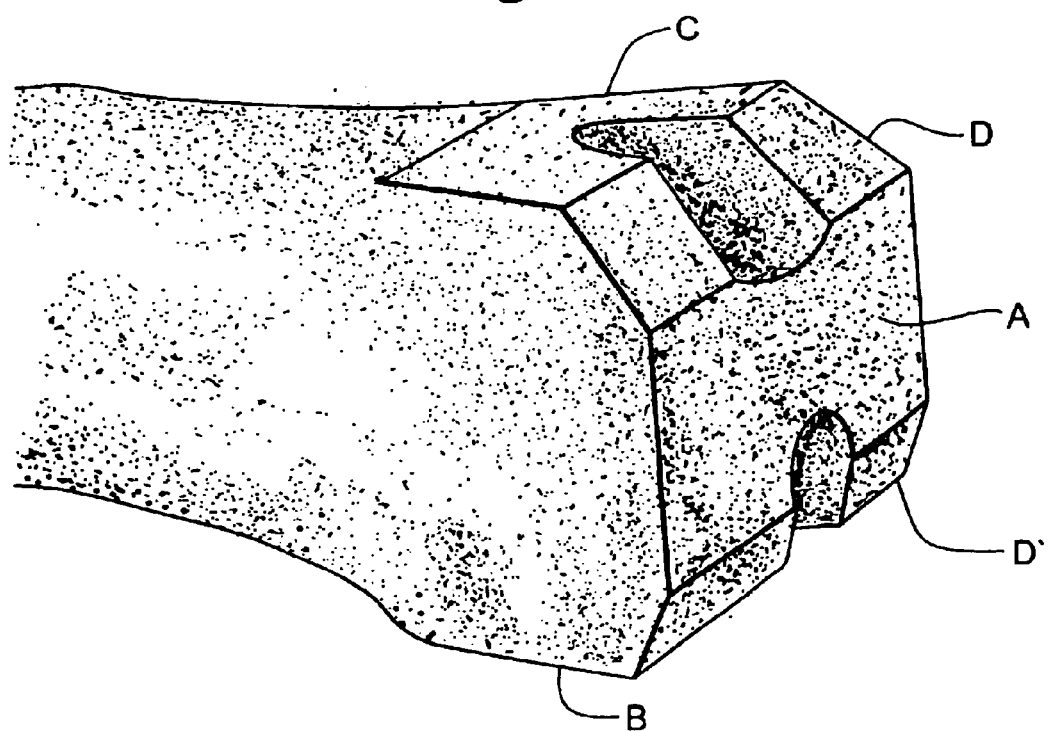
FIG. 1a is a perspective view of a resected distal femur showing facets created in preparation for placement of a knee prosthesis.
Figure 1B:
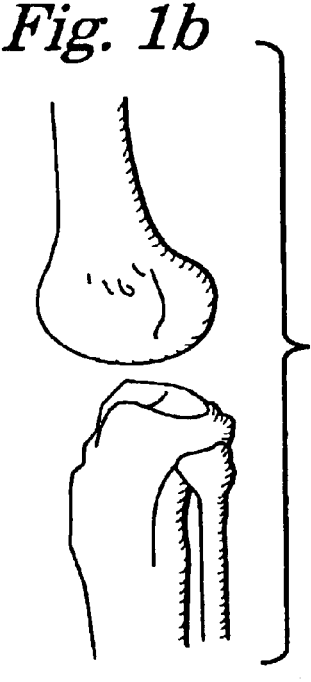
FIG. 1b is a profile view of a distal femur and a proximal tibia uncut.
Figure 1C:
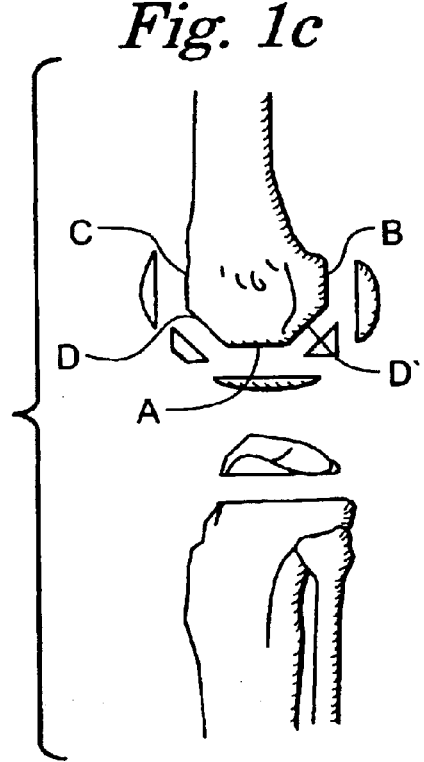
FIG. 1c is a profile view of a resected distal femur and a proximal tibia as faceted for total knee arthroplasty.

The rotating track cutting guide system 30 of the present invention, as depicted in the drawings, generally includes a track subassembly 32 and a variety of bone cutting guides. Bone cutting guides include an anterior and posterior femoral (APF) cutting guide 36, a distal femur and proximal tibia (DFPT) cutting guide 38 and a chamfer cutting guide 40. Track subassembly 32 is adapted to be removably affixed to any of the bone cutting guides. Bone cutting guides are adapted to be removably affixed to bone structures via clamps (not shown), screws (not shown), pins (not shown), drill bits 33 or any other means known to those skilled in the orthopedic arts. Bone cutting guides may be adapted to receive handlebars 35.

Figure 2:
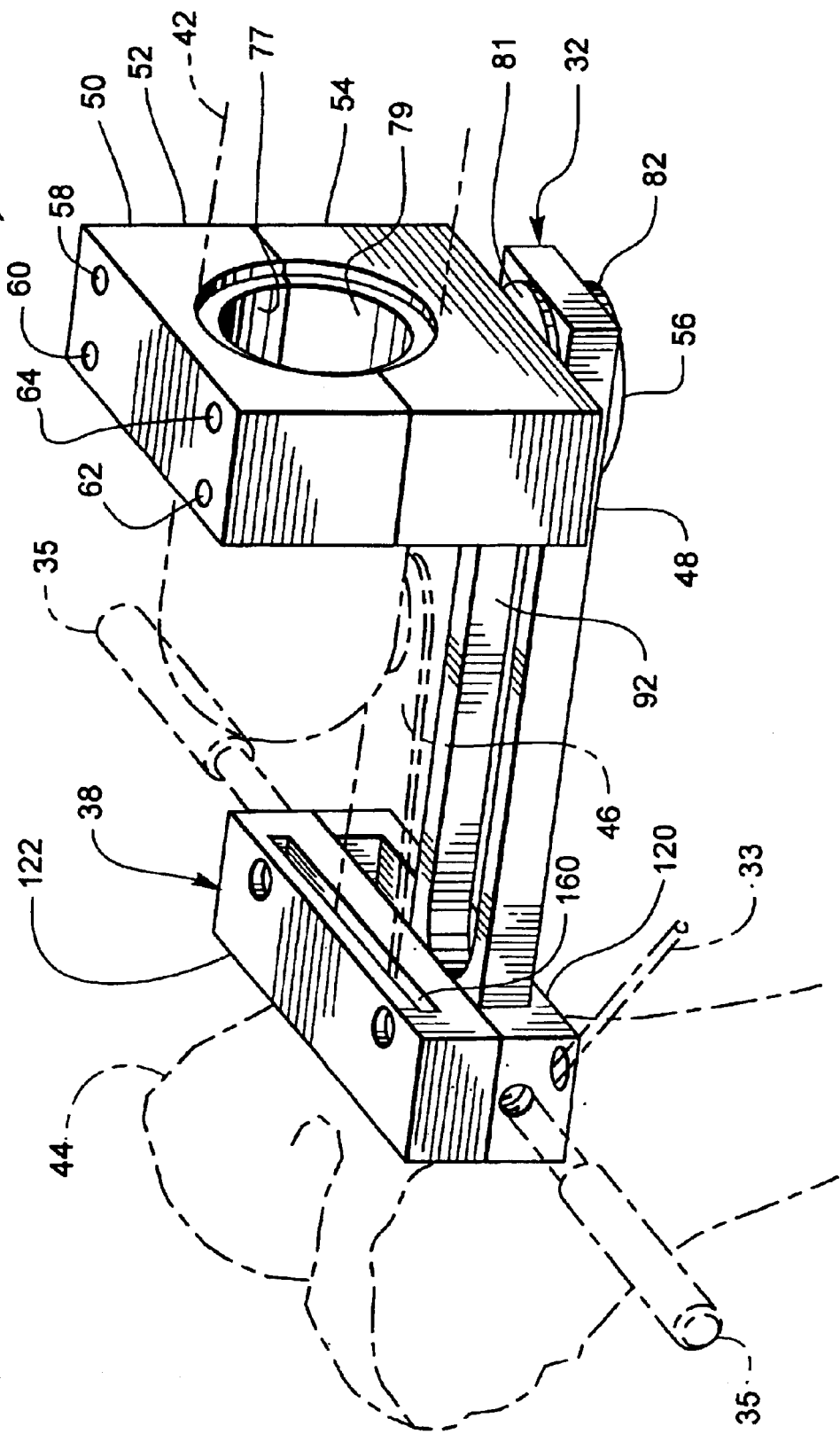
FIG. 2 is a side perspective view of a rotating track cutting guide system of the present invention positioned as attached to a femur, with phantom lines depicting a femur and a saw apparatus.
Figure 4:
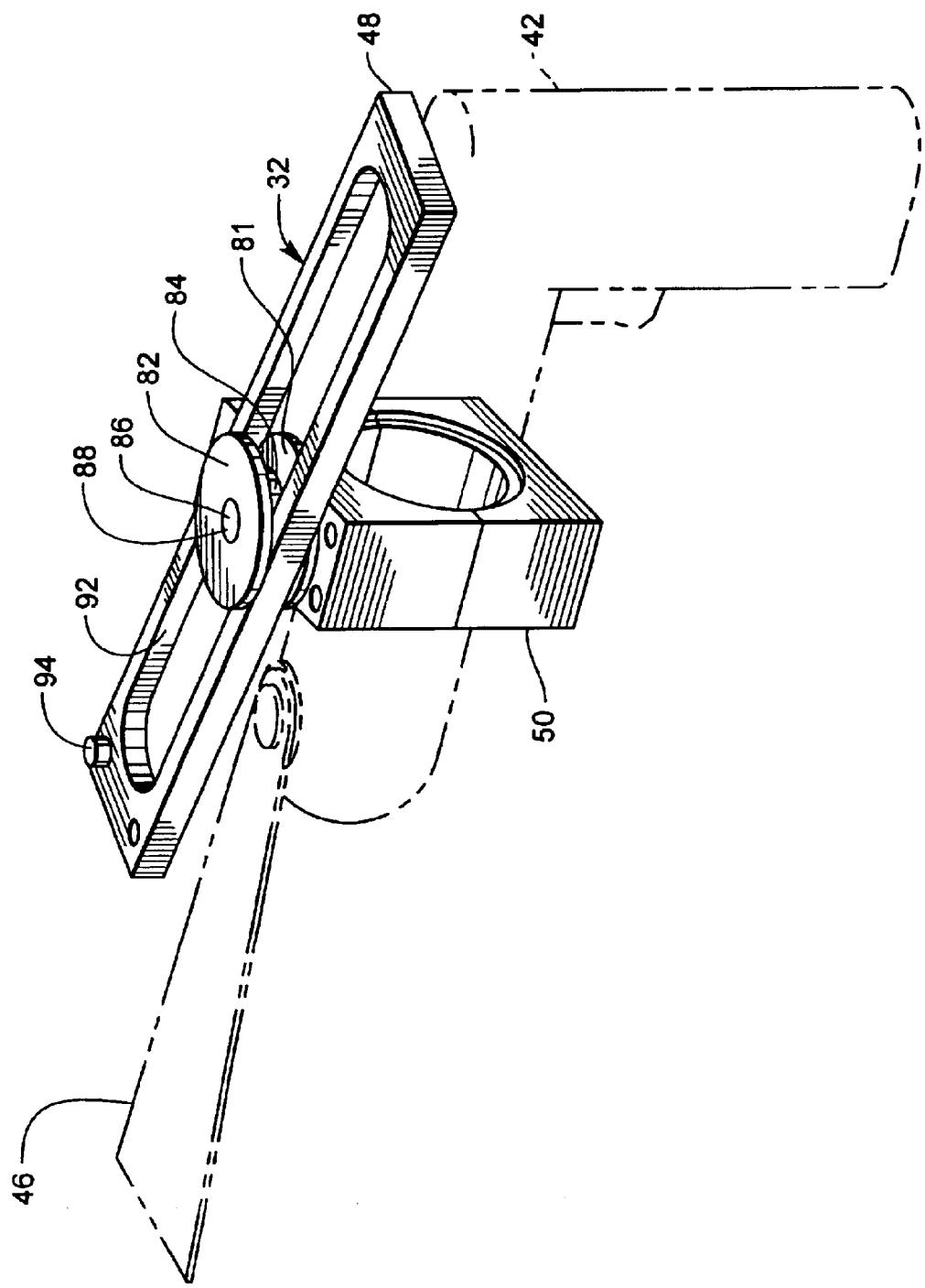
FIG. 4 is a perspective view of the track subassembly as depicted in FIG. 2, but with the subassembly inverted, phantom lines depicting a saw apparatus.

Referring to FIGS. 2, 3 and 4, track subassembly 32 supports an oscillating saw driver 42 and is depicted attached to distal femur and proximal tibia cutting guide 38 which is, in turn, attached to femur 44. Oscillating saw driver 42 drives saw blade 46.

Track subassembly 32 generally includes track 48 and driver carriage 50. Driver carriage 50 is slidably carried on track 48 and is adapted to support oscillating saw driver 42. Oscillating saw driver 42 may be, for example, a 3M oscillating head L120B in combination with a 3M Maxi Driver II L100. Track 48 is adapted to be removably attachable to any of cutting guides 36, 38, 40.

Figure 5:
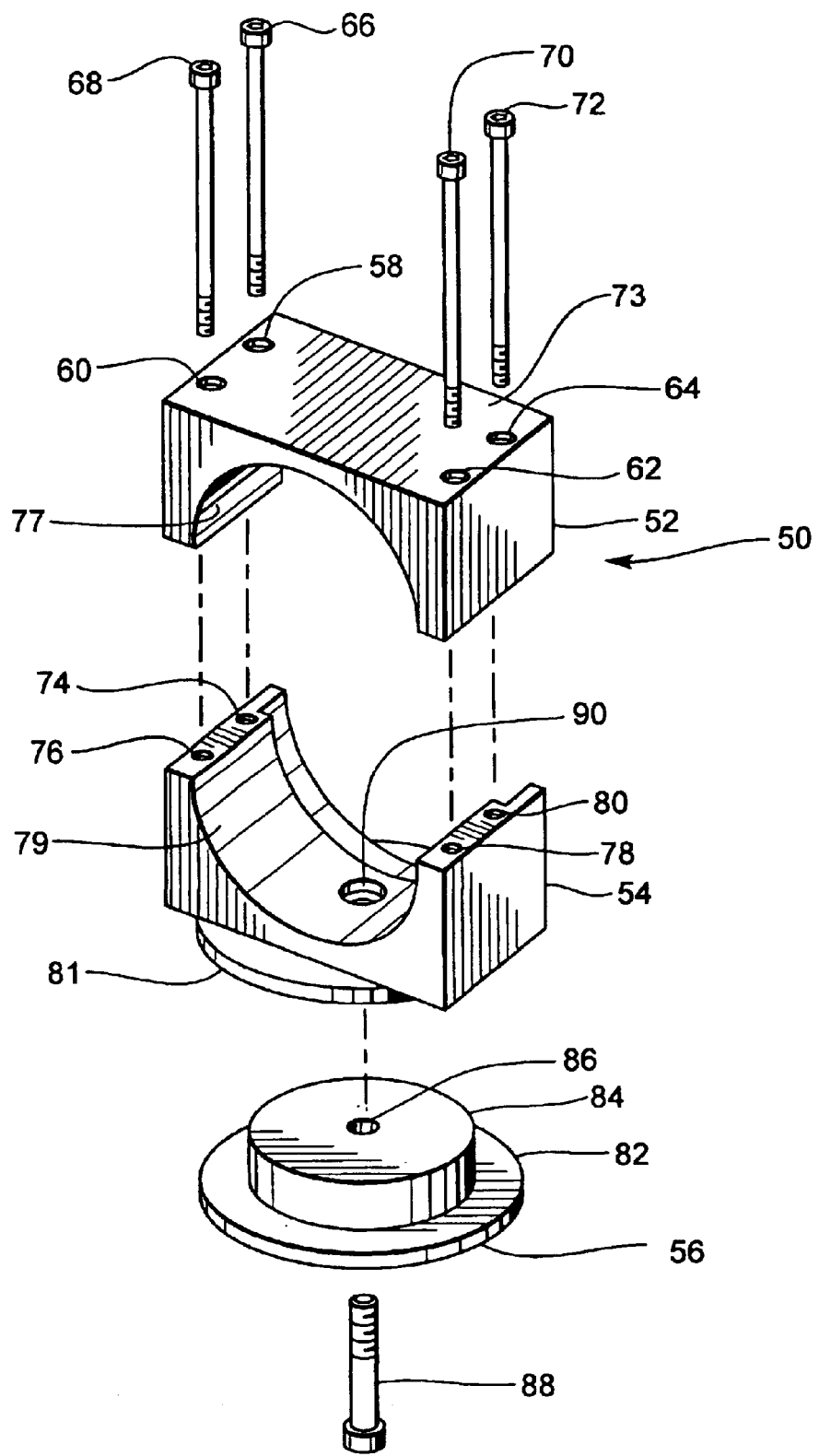
FIG. 5 is an exploded top perspective view of a driver carriage used in accordance with the present invention.

Referring to FIG. 5, driver carriage 50, includes superior driver brace 52, inferior driver brace 54 and endcap 56.

Superior driver brace 52 presents counterbored holes 58, 60, 62, 64 adapted to receive threaded fasteners 66, 68, 70, 72 through top brace face 73. Threaded fasteners 66, 68, 70, 72 thread into fastening holes 74, 76, 78, 80 in inferior driver brace 54, to secure superior driver brace 52 to inferior driver brace 54. Inner brace contact surfaces 77, 79 of superior driver brace 52 and inferior driver brace 54 conform to oscillating saw driver 42.

Endcap 56 includes superior circular plate 81, inferior circular plate 82 and cylindrical spacer 84. Inferior circular plate 82 presents counterbored hole 86 adapted to receive threaded fastener 88. Counterbored hole 86 is located proximate the center of inferior circular plate 82. Threaded fastener 88 is receivable into threaded bore 90 located in inferior driver brace 54.

Referring particularly to FIG. 3, track 48 presents track slot 92, alignment peg 94, and counterbored alignment hole 96 adapted to receive fastener 97. Track 48 further presents superior track face 98, inferior track face 100, front track face 102, back track face 104, inner track face 106 and side track faces 108. Track slot 92, as defined by inner track faces 106, is of appropriate width to slidably receive cylindrical spacer 84. The thickness of track 48, as defined as the distance between superior track face 98 and inferior track face 100, is adapted to be received between superior circular plate 80 and inferior circular plate 82.

Front end 110 of track 48 is adapted to be secured to bone cutting guides 36, 38, 40. Front end 110 includes alignment peg 94 and counterbored alignment hole 96. Counterbored alignment hole 96 receives threaded fastener 97. In another embodiment, depicted in FIG. 3a, front end 110' includes alignment pins 114, recesses 116 and alignment clips 118.

Referring to FIG. 6, distal femur and proximal tibia cutting guide 38 generally includes positioning guide 120 and cutting guide 122. DFPT cutting guide 38 is adapted to receive track 48.

Positioning guide 120 presents attachment shelves 124, 126, peg holes 128, 130, track fastening holes 132, 134, pin holes 136, 138, diagonal pin holes 144, 146, handlebar holes 148, 150, and guide fastening holes 152, 154. Guide fastening holes 152, 154 are adapted to receive guide fasteners 156, 158.

Figure 6A:
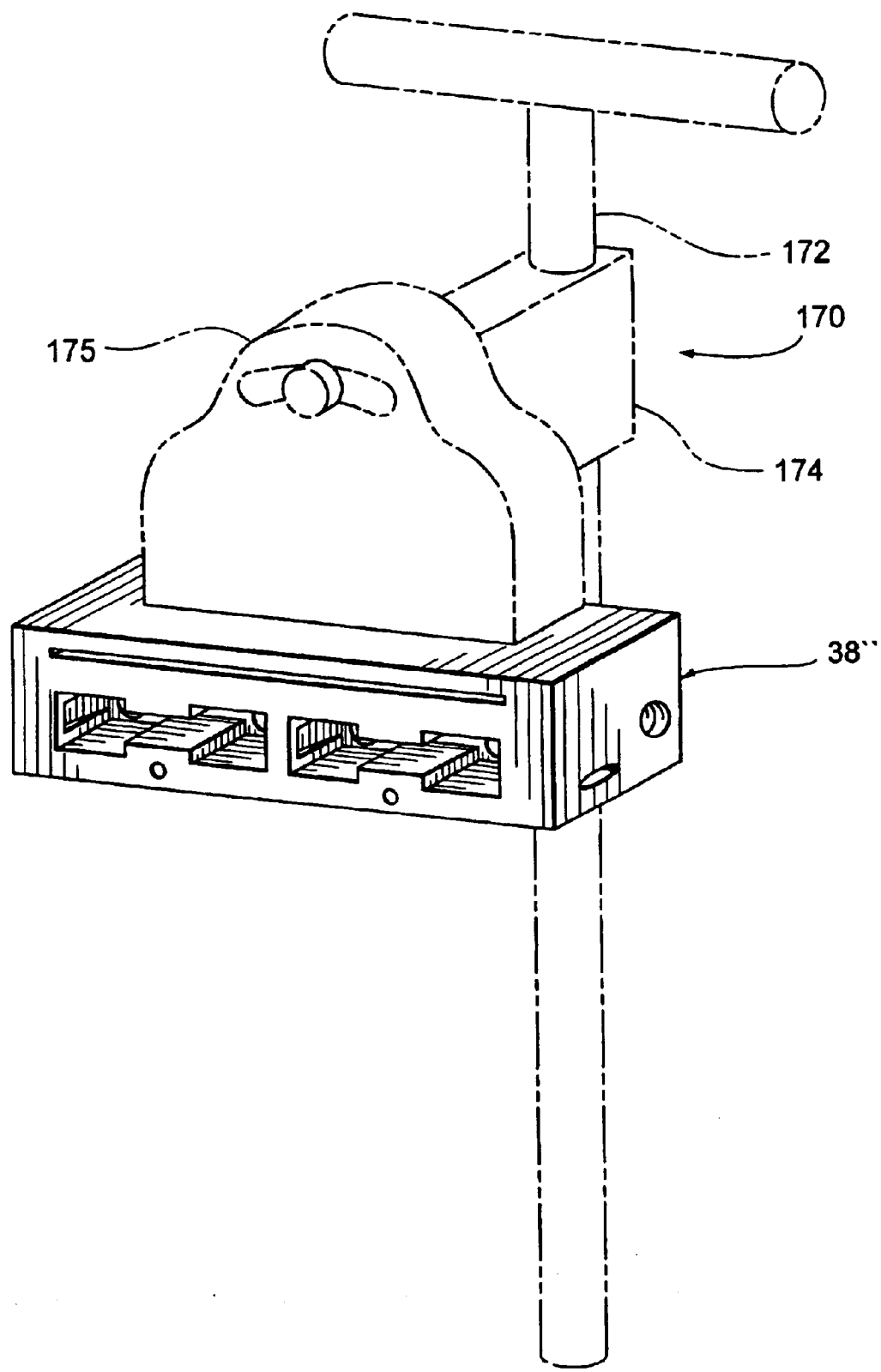
FIG. 6a is a perspective view of an alternative embodiment of a distal femur and proximal tibia cutting guide, attached to an intramedullary alignment system (depicted in phantom)

Cutting guide 122 presents cutting slot 160, intramedullary attachment holes 162, 164 and counterbore guide holes 166, 168. Also shown in phantom in FIG. 6a is intramedullary alignment system 170. Intramedullary alignment system 170 includes intramedullary alignment rod 172, bracket 174 and angle positioner 175.

Figure 16:
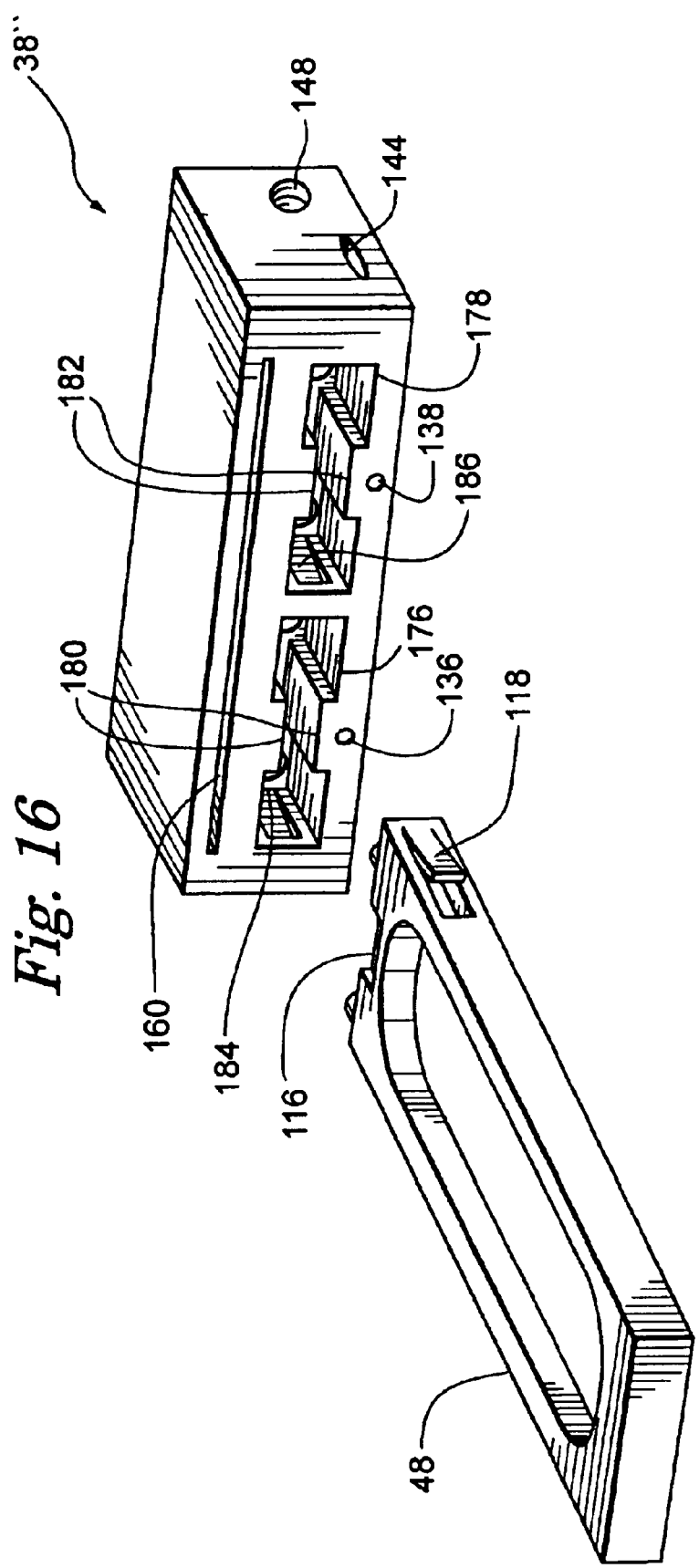
FIG. 16 is a perspective view of an alternative embodiment of a distal femur and proximal tibia cutting guide and track in accordance with the present invention.

Referring to FIG. 16, another embodiment of DFPT cutting guide 38" is shown. This embodiment of DFPT cutting guide 38" presents attachment slots 176, 178, attachment bosses 180, 182, and attachment clip receivers 184, 186. This embodiment further presents diagonal pin holes 144 and handlebar holes 148 and slot 160 similar to the initial embodiment.

Figure 7:
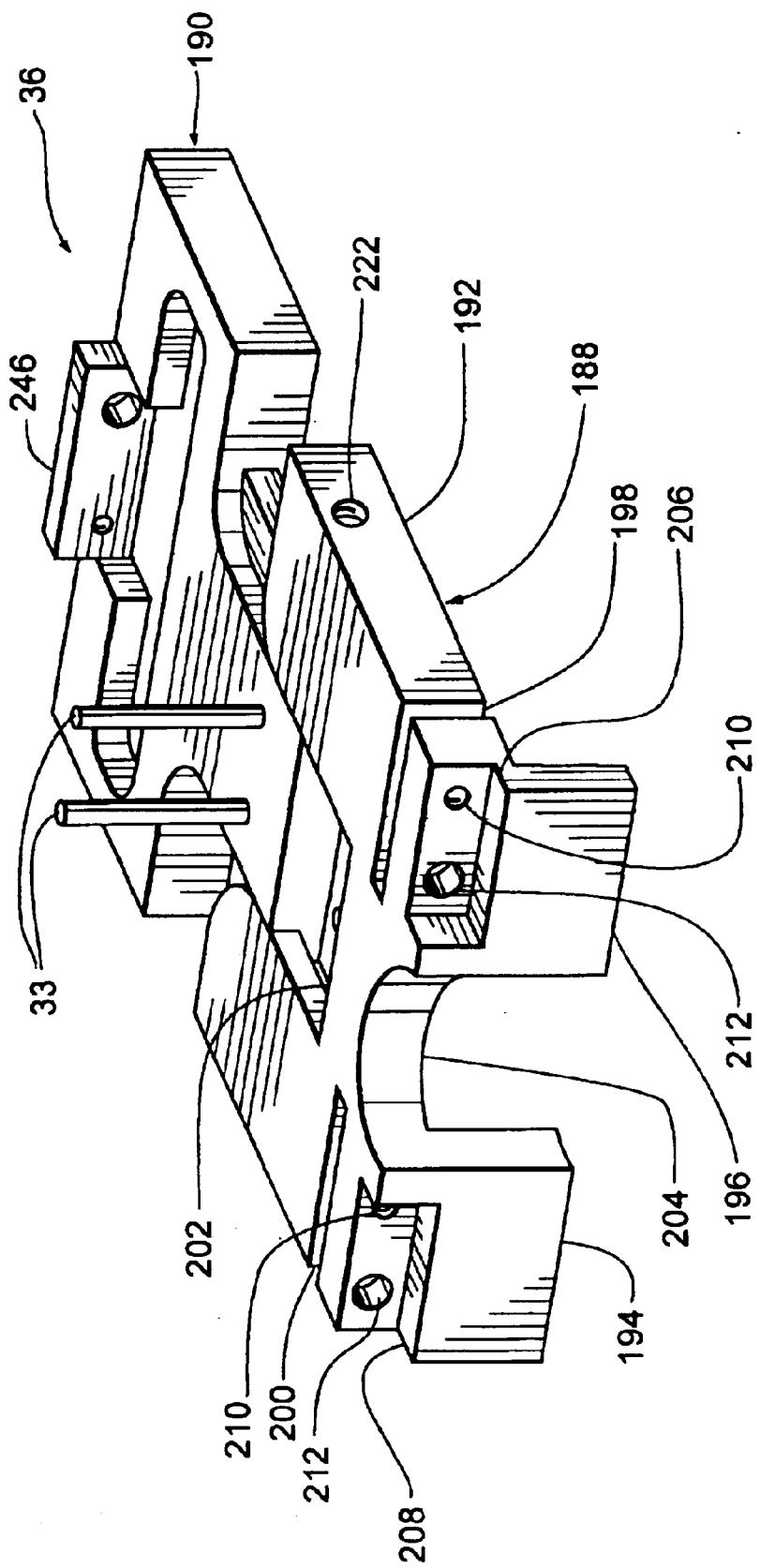
FIG. 7 is rear perspective view of an anterior and posterior femoral cutting guide subassembly in accordance with the present invention.

Referring to FIG. 7, APF cutting guide 36 generally includes posterior cutting guide 188 and anterior cutting guide 190. Posterior cutting guide 188 generally includes body 192 and posterior condyle referencing paddles 194, 196.

Figure 8:
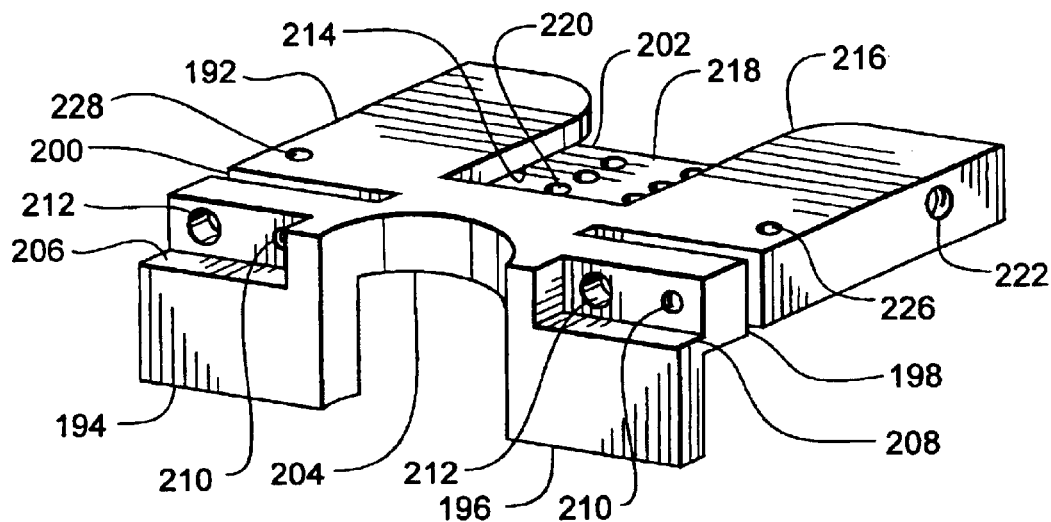
FIG. 8 is top perspective view of a posterior cutting guide in accordance with the present invention.
Figure 9:
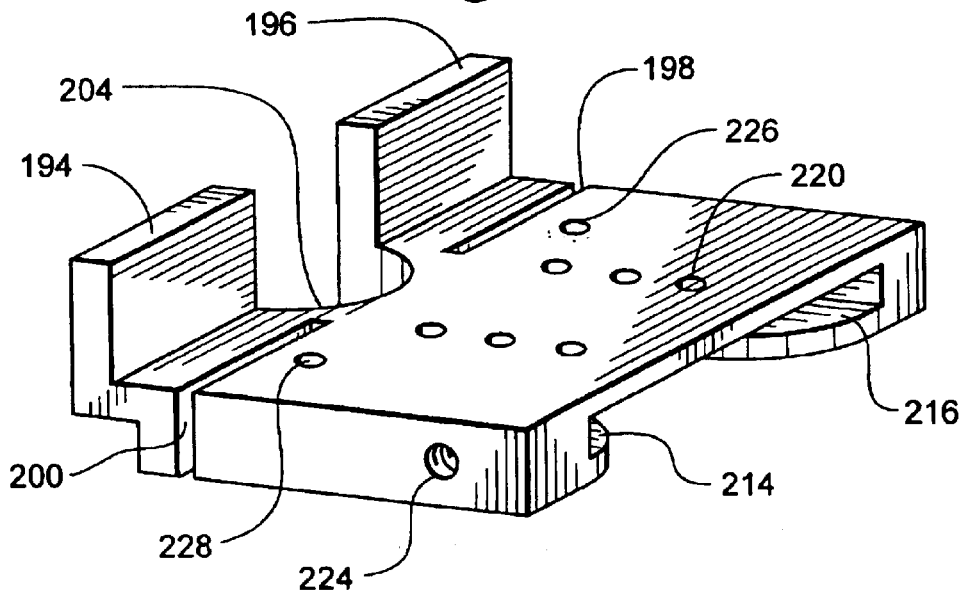
FIG. 9 is a bottom perspective view of the posterior cutting guide in accordance with the present invention.

Referring particularly to FIGS. 8 and 9, body 192 presents condyle cutting slots 198, 200, sizing slot 202 and notch 204. Notch 204 is located between posterior condyle referencing paddles 194, 196. Attachment shelves 206, 208 are located at the juncture between posterior condyle referencing paddles 194, 196 and body 192. Each attachment shelf 206, 208 further includes fastening holes 210 and peg holes 212. Attachment shelves 206, 208 are adapted to receive track 48.

Sizing slot 202 includes inner sizing slot grooves 214, 216 and inner sizing slot top face 218. Inner sizing slot top face 218 presents a plurality of sizing holes 220. Body 192 further presents handlebar attachments 222, 224 and diagonal fixation pinholes 226, 228 oriented diagonally inward therethrough.

Figure 10:
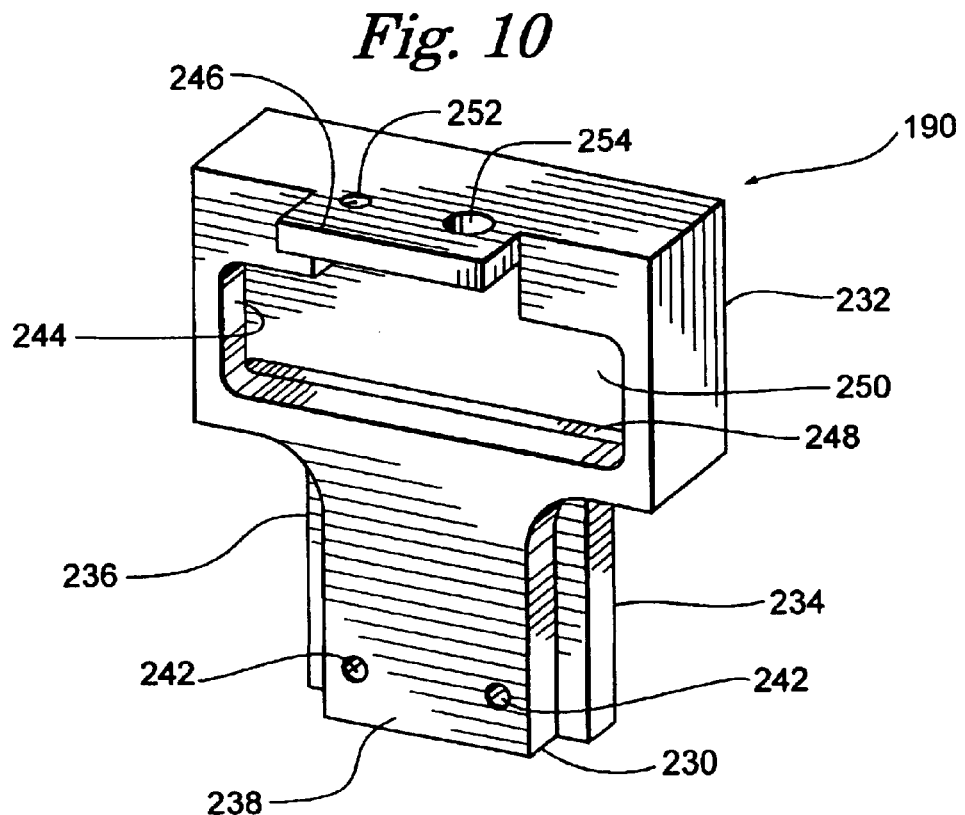
FIG. 10 is a front perspective view of an anterior cutting guide in accordance with the present invention.
Figure 11:
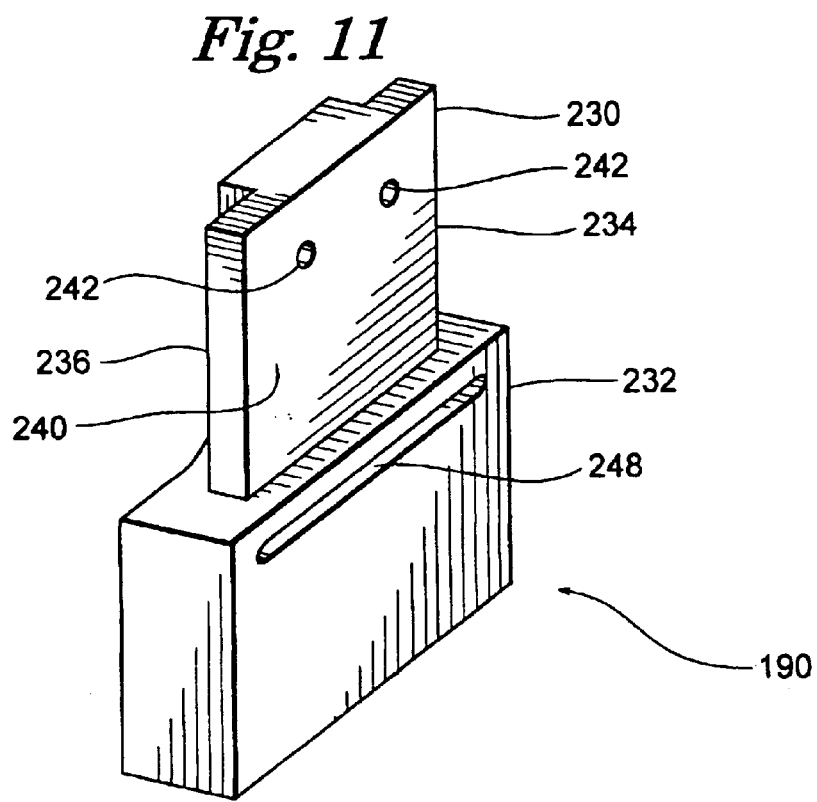
FIG. 11 is rear perspective view of the anterior cutting guide in accordance with the present invention.
Figure 12:
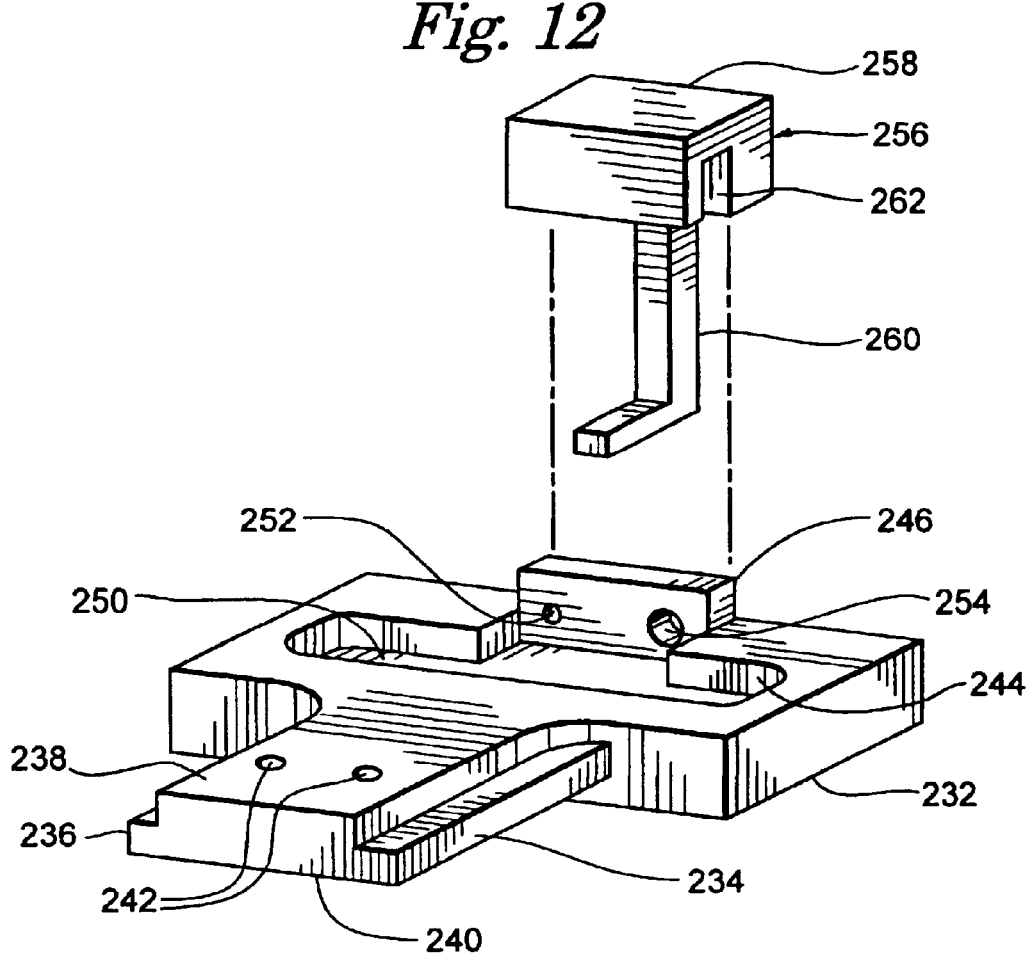
FIG. 12 is an exploded, top perspective view of the anterior cutting guide with the detachable femoral anterior reference in accordance with the present invention.

Referring to FIGS. 10, 11 and 12, anterior cutting guide 190 generally includes sizing ledge 230 and guide body 232. Sizing ledge 230 generally includes sizing side ridges 234, 236, sizing ledge top face 238 and sizing ledge bottom face 240. Sizing ledge top face 238 presents sizing holes 242 therethrough. Sizing ledge 230 is dimensioned so as to be slidably received into sizing slot 202 as depicted in FIGS. 8 and 9.

Guide body 232 includes inner ring 244 and attachment ledge 246. In a first embodiment of anterior cutting guide 190, inner ring 244 is cut entirely through the thickness of guide body 232. In a second embodiment inner ring 244 is cut partially through the thickness of guide body 232, and a cutting slot 248 is cut through the remaining thickness. In the second embodiment attachment buttress 250 is present.

Attachment ledge 246 includes fastening hole 252 and peg hole 254. Attachment ledge 246 is adapted to receive track 48.

Figure 13:
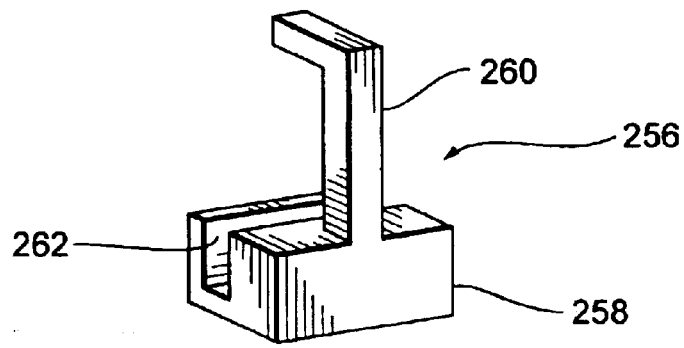
FIG. 13 is a bottom perspective view of the detachable anterior reference in accordance with the present invention.

Attachment ledge 246 is also adapted to receive detachable femoral reference 256. Referring to FIG. 13, detachable femoral reference 256 generally includes body 258, L-bracket 260 and attachment slot 262.

Figure 14:
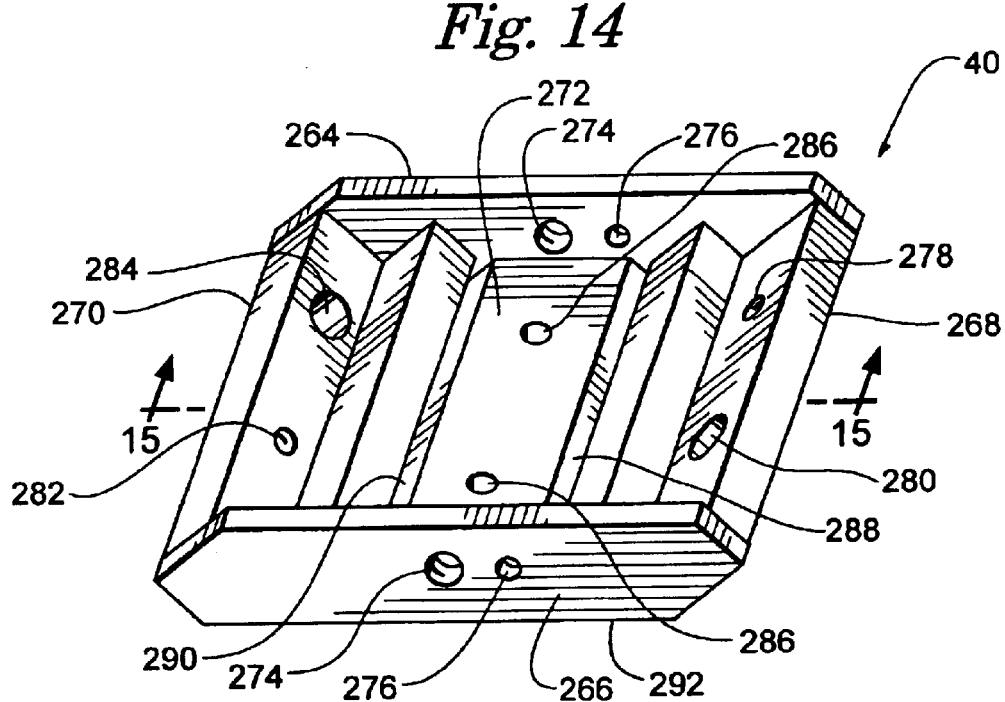
FIG. 14 is a top perspective view of a chamber cutting guide subassembly in accordance with the present invention.
Figure 15:
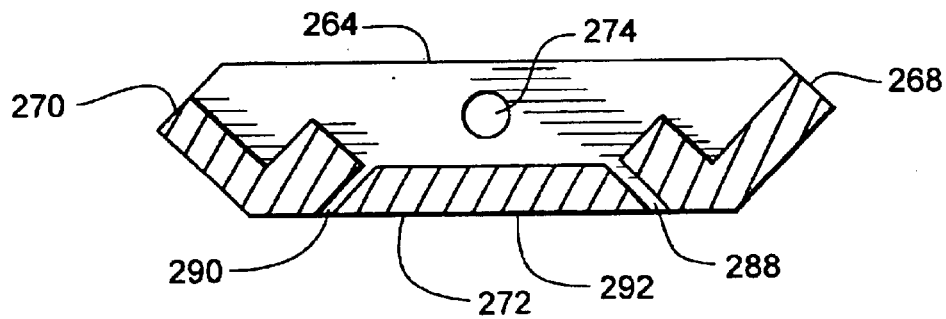
FIG. 15 is a cross-sectional view of the chamfer cutting guide subassembly of the present invention taken along line 15—15 of FIG. 14.

Referring to FIGS. 14 and 15, chamfer cutting guide 40 generally includes side plates 264, 266, attachment guide plates 268, 270 and central guide plate 272. Side plates 264, 266 each present handlebar hole 274 and diagonal fixation hole 276. Attachment guide plate 268 presents anterior fastening hole 278 and anterior peg hole 280. Attachment guide plate 270 presents posterior fastening hole 282 and posterior peg hole 284. Central guide plate 272 presents a plurality of guide positioning holes 286. Attachment guide plate 268 and central guide plate 272 define anterior cutting slot 288. Attachment guide plate 270 and central guide plate 272 define posterior cutting slot 290. Bottom side attachment guide plates 268, 270 and central guide plate 272 define bone contacting face 292.

Figure 17:
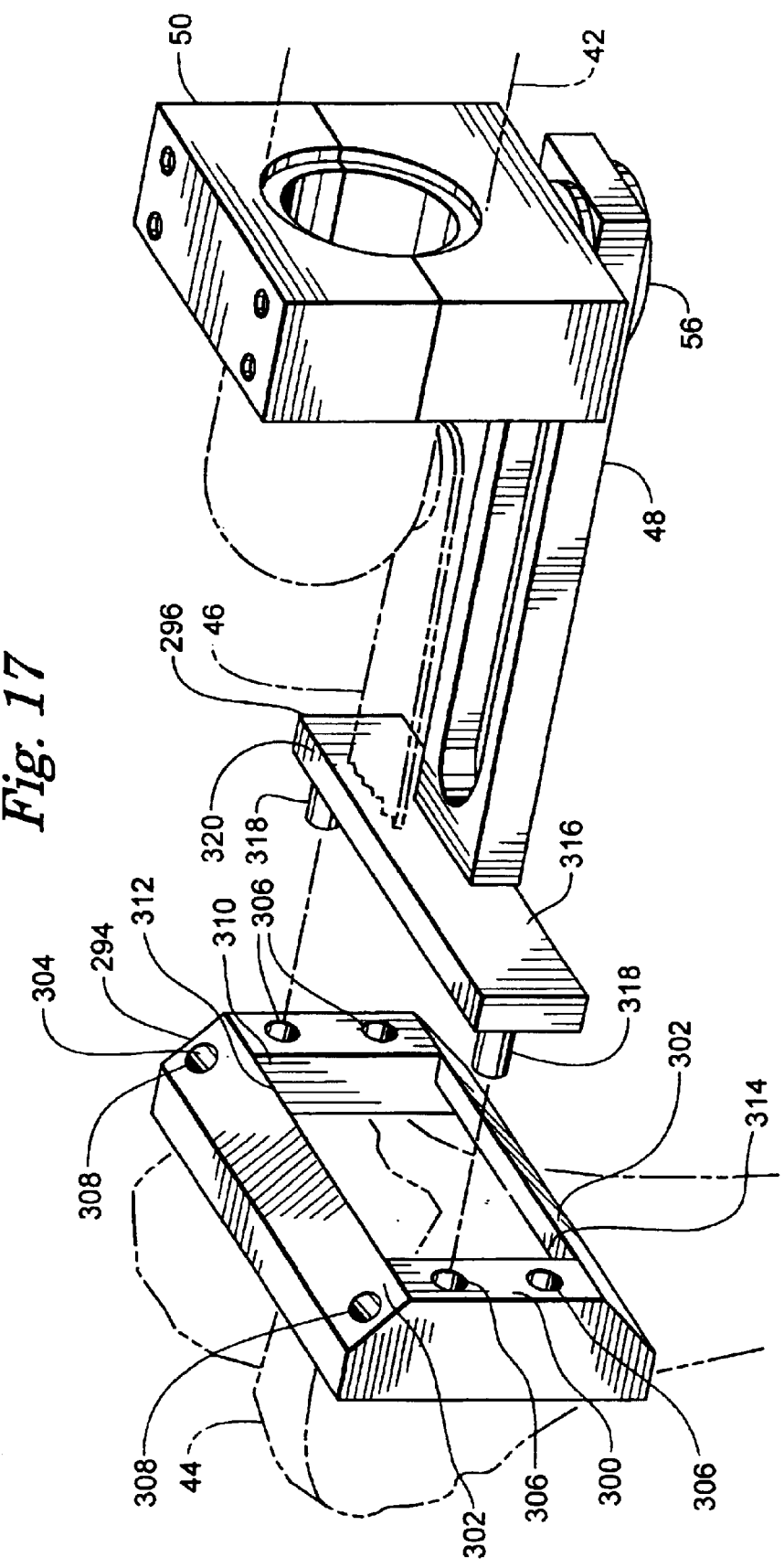
FIG. 17 is a perspective view of a first alternative embodiment of the rotating track cutting guide system including a multipurpose cutting guide and multipurpose track, with phantom lines depicting a bone saw and a femur.
Figure 18:
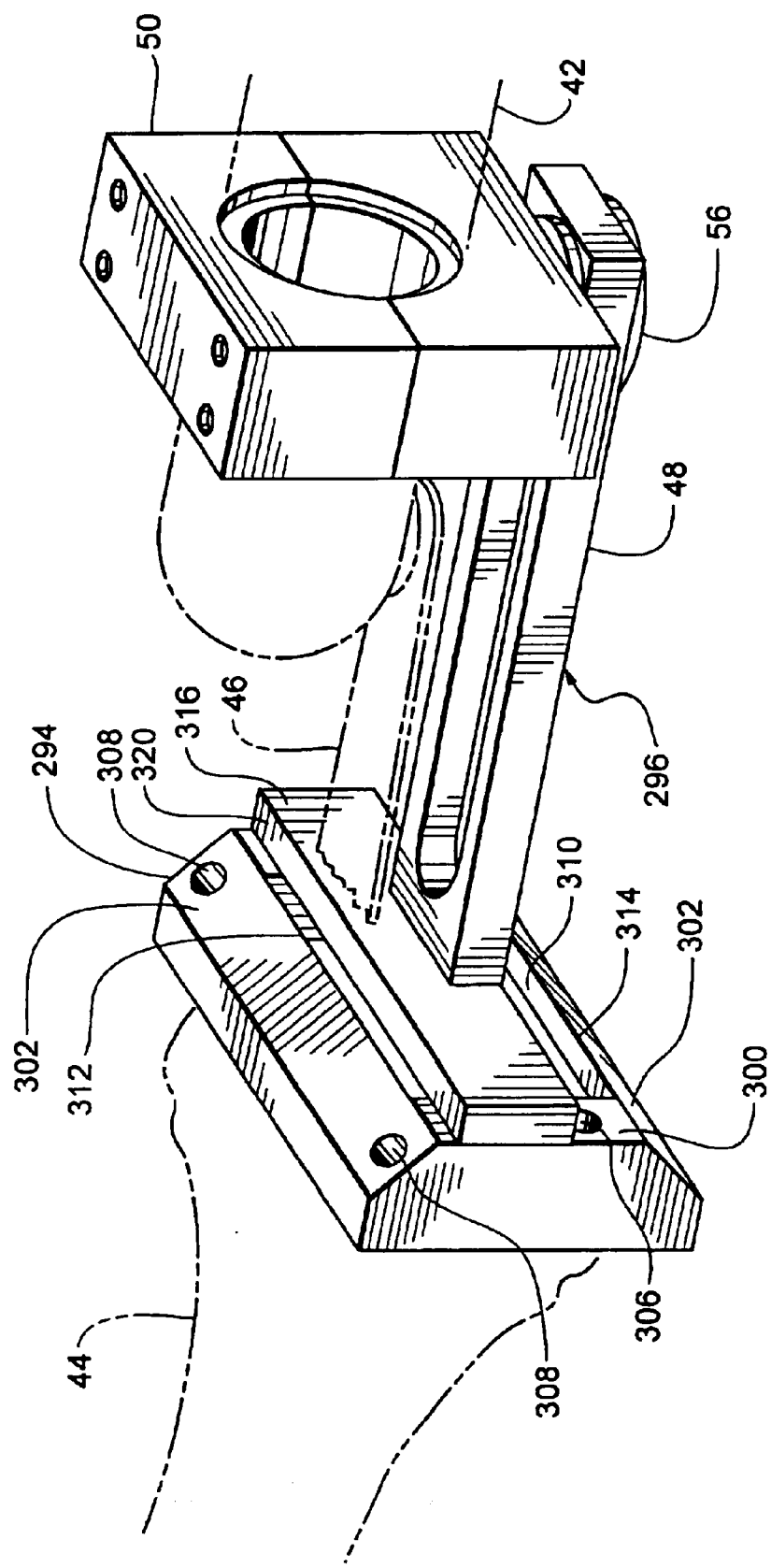
FIG. 18 is a perspective view of the multipurpose cutting guide and multipurpose track of FIG. 17 assembled, with phantom lines depicting a bone saw and a femur.

Referring to FIGS. 17 and 18, another embodiment of rotating track cutting guide system 30 is depicted. This embodiment generally includes multipurpose cutting guide 294 and multipurpose track 296.

Multipurpose cutting guide 294 is generally an open frame guide. Multipurpose cutting guide 294 includes perpendicular cut adaptor 300 and chamfer cut adaptors 302. Multipurpose cutting guide 294 defines a plurality of alignment rod receivers 304. Perpendicular cut adaptor 300 includes perpendicular rod receivers 306. Chamfer cut adaptors 302 include chamfer rod receivers 308. Multipurpose cutting guide 294 defines a window 310. Window 310 has a superior edge 312 and an inferior edge 314.

Multipurpose track 296 is generally similar to track 48 except for the addition of a terminal block 316 secured at the end thereof. Terminal block 316 supports alignment rods 318 and presents upper edge 320. In one embodiment, depicted in FIG. 19 terminal block 316 also is perforated by guide slot 322. Guide slot 322 is sized to receive saw blade 46.

Figure 22:
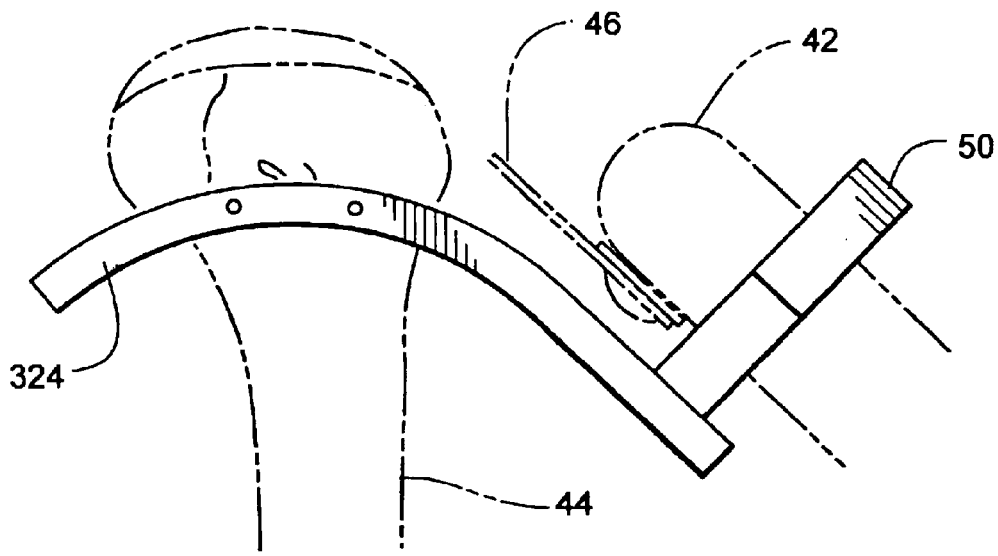
FIG. 22 is a profile view of a third alternative embodiment of the rotating track cutting guide system engaged to a femur.
Figure 23:
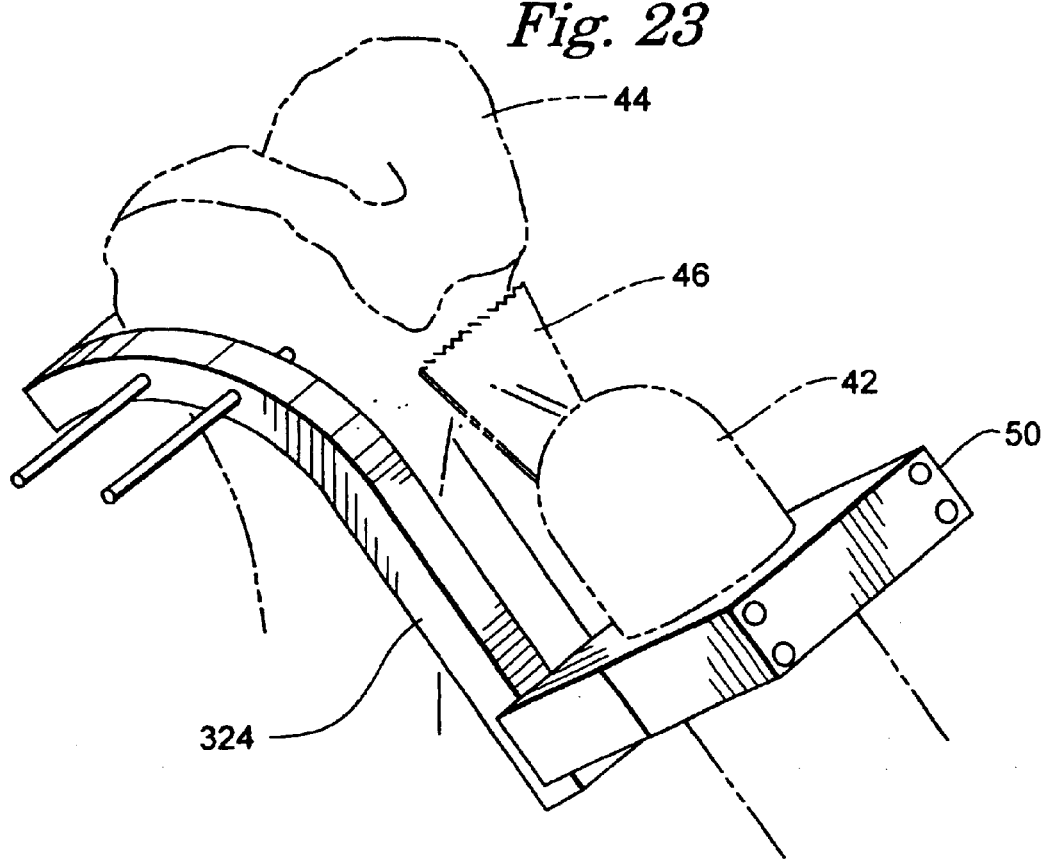
FIG. 23 is a perspective view of the embodiment of FIG. 22 with a bone saw and a femur depicted in phantom.

Referring to FIGS. 22 and 23, an additional embodiment of the present invention includes curved track 324. Driver carriage 50 is slidably and rotatably retained on curved track 324. Otherwise this embodiment is similar in structure to the foregoing embodiments.

In operation, rotating track cutting guide system 30 is assembled in concert with oscillating saw driver 42. Referring to FIG. 5, superior driving brace 52 and inferior driving brace 54 are separated and assembled to grip oscillating saw driver 42 as depicted in FIG. 4. Saw blade 46 is attached to oscillating saw driver 42. Track 48 may then be connected to any of bone cutting guides 36, 38, 40.

Referring particularly to FIGS. 2 and 6, in preparing to make an initial cut on femur 44, distal femur and proximal tibia cutting guide 38 is secured to femur 44 via clamps, screws, pins or drill bits or any other means known in the orthopedic arts. If desired, handle bars 35 may be secured to DFPT cutting guide 38 to allow an assistant to the surgeon to help support DFPT cutting guide 38 during the cutting process. Track 48 is secured to DFPT cutting guide 38 prior to cutting.

Referring particularly to FIG. 6, DFPT cutting guide 38 may be disassembled into positioning guide 120 and cutting guide 122. For attachment, front end 110 of track 48 is inserted so that it rests on one of attachment shelves 124, 126 and so that alignment peg 94 engages into peg hole 128, 130. Thereupon, a fastener 131 may be inserted through counterbored alignment hole 96 and threaded into track fastening hole 132, 134. Once fastener 131 is tightened in place, cutting guide 122 is assembled to positioning guide 120. This is achieved by inserting fasteners 156, 158 through cutting guide counterbored holes 166, 168 on cutting guide 122 and tightening fasteners 156, 158 against fastening holes 152, 154.

Referring again to FIGS. 2, 3 and 4, oscillating saw driver 42 may then be moved linearly and rotationally in a fixed plane because of the interaction between driver carriage 50 and track 48. End cap 56 is securely and slidably engaged to track slot 92, thereby allowing driver carriage 50, along with oscillating saw blade 46, to move within a fixed plane aligned with cutting slot 160 if present.

Oscillating saw driver 42 may then be advanced through cutting slot 160 in order to make an initial planar cut across the inferior end of femur 44. Because of the interconnection of rotating track cutting guide system 30 to femur 44, this cut will be planar and smooth.

After this initial cut is made, distal femur and proximal tibia cutting guide 38 may be unfastened from femur 44 and removed.

Making the initial femoral cut with the alternate embodiment of DFPT cutting guide 38 depicted in inset 3a and FIG. 16 requires a slightly different procedure. In this embodiment, positioning guide 120 and cutting guide 122 are combined into a single unit. DFPT cutting guide 38 is secured to femur 44 by the insertion of drill bits 33 into fastening holes 136, 138. Track 48 is then inserted into attachment slot 176, 178, and alignment of track 48 is achieved through the interaction of attachment bosses 180, 182 with recesses 116. Upon insertion, alignment clips 118 engage attachment clip receivers 184, 186 to secure track 48 to DFPT cutting guide 38. Thereafter, the initial femoral cut is made as described above.

Referring to FIGS. 7–12, anterior and posterior femoral cutting guide 36 is adapted to be placed against the planar resected bone surface previously produced by the use of DFPT cutting guide 38. To properly orient APF cutting guide 36, body 192 is placed on the resected bone surface so that posterior condyle referencing paddles 194, 196 are in contact with the condyles on femur 44 and notch 204 is aligned with the intercondylar notch on femur 44.

After properly orienting anterior and posterior femoral cutting guide 36, the size of femur 44 may be measured using detachable femoral reference 256. Detachable femoral reference 256 is placed so that attachment slot 262 engages attachment ledge 246. The femur 44 may then be sized by pressing posterior condyle referencing paddles 194, 196 against the femoral condyles and pressing L-bracket 260 of detachable femoral reference 256 against the anterior femoral surface.

Thereafter, APF cutting guide 36 is secured to femur 44 by any means known to the orthopedic arts. If necessary, handlebars 35 may be secured to handlebar attachments 222, 224 to enable an assistant to hold and restrain the motion of APF cutting guide 36 to provide additional stability during the cutting process.

Resection of the anterior portion of femur 44 may then be accomplished. Track subassembly 32 is secured to attachment ledge 246. Oscillating saw driver 42 may then be advanced along track 48 to make the appropriate cut to the anterior region of femur 44.

Resection of the posterior portion of the femoral condyles is accomplished by sequentially securing track subassembly 32 to attachment shelves 206, 208. Oscillating saw driver 42 may then be advanced and rotated along track 48 as needed to accomplish the required posterior femoral condyle cuts. Once the required resections are made, APF cutting guide 36 is removed from femur 44.

Next, referring to FIGS. 14 and 15, anterior and posterior chamfer cuts may be made to femur 44. Chamfer cutting guide 40 is secured to the resected surface of femur 44 by use of any means known to the orthopedic art such that bone contacting face 292 is flush with the resected femur surface A. Track subassembly 32 is then secured to one of attachment guide plates 268, 270. To make the posterior chamfer cut, track subassembly 32 is secured at anterior peg hole 280 and anterior fastening hole 278. Oscillating saw driver 42 may then be advanced along track 48 and rotated as need be to make the required resection. The anterior chamfer cut is made in a similar fashion, attaching track subassembly 32 at posterior peg hole 284 and posterior fastening hole 282. If desired, handlebars 35 may be secured at handlebar holes 274 in order to provide additional stabilization of chamfer cutting guide 40.

To effect resection of the proximal portion of the tibia, a procedure similar to that used for resecting the distal portion of femur 44 is followed.

Figure 19:
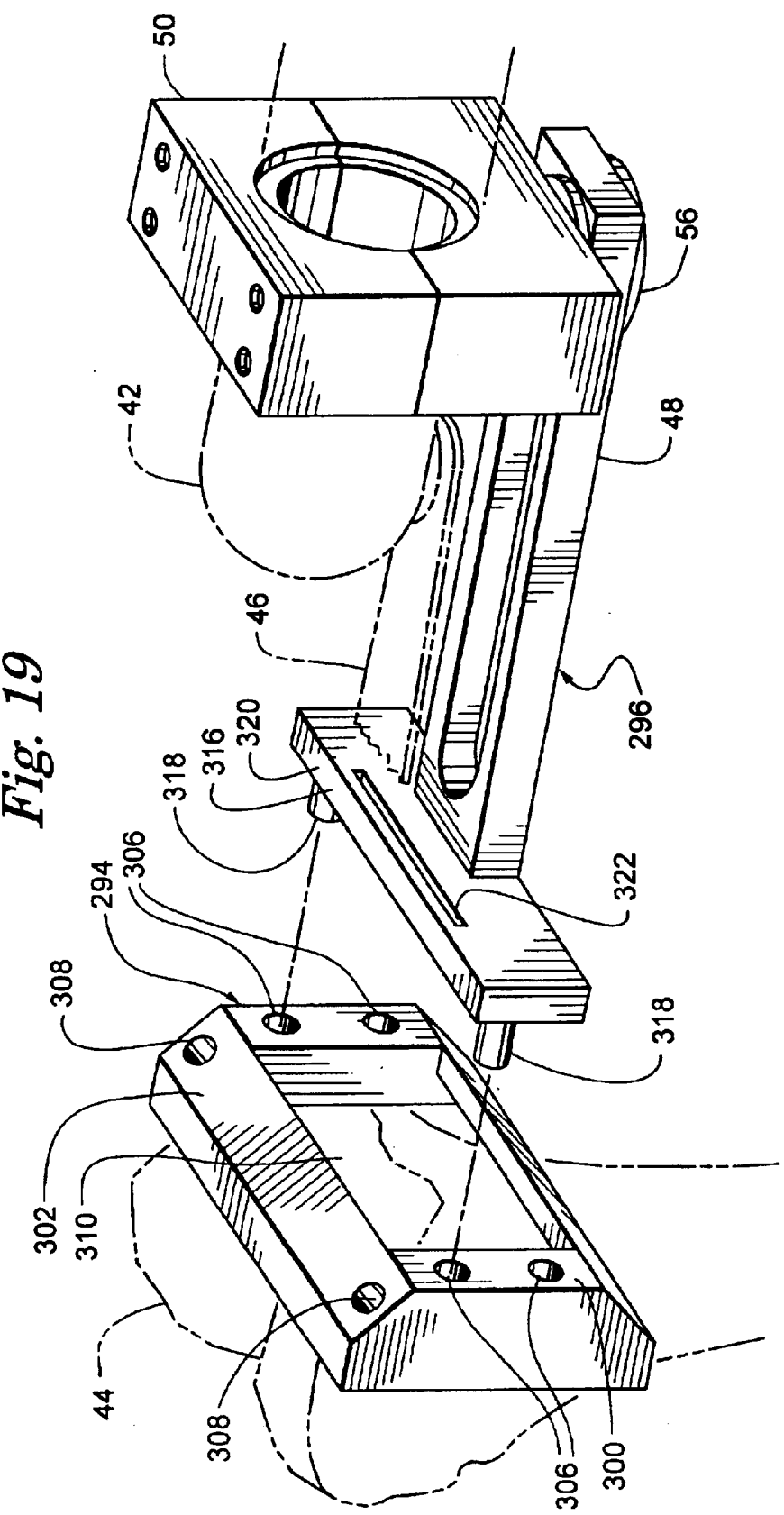
FIG. 19 is a perspective view of a second alternative embodiment of the multipurpose track subassembly in accordance with the present invention, with phantom lines depicting a bone saw and a femur.

Referring to FIGS. 17 and 19, to utilize multipurpose cutting guide 294 for the initial femoral cut, multipurpose cutting guide 294 is secured to the anterior surface of femur 44 by any means known to the orthopedic arts. Note that the presence of window 310 provides convenient visibility of the bone structure for the surgeon.

Once multipurpose cutting guide 294 is in position, multipurpose track 296 may be engaged to multipurpose cutting guide 294 as depicted in FIG. 18. Thereupon, oscillating saw driver 42 and saw blade 46 may be advanced along multipurpose track 296 in order to make the appropriate cuts.

Note, referring to FIG. 18, that when engaged, terminal block 316 and superior edge 312 combine to form an effective guide slot for saw blade 46. In another alternate embodiment, depicted in FIG. 19, terminal block 316 includes guide slot 322 to provide additional stabilization of saw blade 46.

After making the initial femoral cut, as depicted in FIG. 17, multipurpose cutting guide 294 may be relocated to make anterior and posterior femoral cuts. This orientation is depicted in FIG. 18. After multipurpose cutting guide 294 is secured to femur 44 at the location of the initial femoral cut, multipurpose track 296 may be engaged to make the anterior femoral cut. Once the anterior femoral cut is completed, multipurpose track 296 may be removed, rotated 180°, around the longitudinal axis of multipurpose track 296 and replaced on multipurpose cutting guide 294 in order to make the posterior femoral cut.

After the posterior femoral cut is made, multipurpose track 296 may be removed and relocated so as to engage chamfer cut adaptor 302 in order to make a first chamfer cut. Thereafter, multipurpose track 296 may be located to the other chamfer cut adaptor 302 in order to make the second chamfer cut to this resected femur 44.

Note that when placed on chamfer cut adaptors 302, upper edge 320 of terminal block 316 provides support for saw blade 46 and superior edge 312 or inferior edge 314 also provide support for saw blade 46. This additional support serves to improve the planar quality of the cuts made.

Multipurpose cutting guide 294 both reduces the number of parts necessary for the rotating track cutting guide system 30 and allows the anterior and posterior femoral cuts as well as the chamfer cuts to be made without the necessity of repositioning or replacing the cutting guide.

EXAMPLES

A quantitative assessment of the final design of the rotating track cutting guide system was performed to judge its effectiveness. Its capabilities were compared to cutting guides from a typical knee replacement system, the Exodus® System (Orthopaedic Innovations, Minneapolis, Minn.). Three experiments were performed to appraise the efficacy of the rotating track cutting guide system. The following experiments were performed:

A. Precision Analysis: Evaluated the each system's capacity to reproducibly cut in the same plane.

B. Blade Wear Analysis: Examined the cutting guides' success at reducing blade wear.

C. Femoral Component Fit Analysis: Provided information on the amount of contact between prosthesis and the resected bone surface to determine the accuracy with which the cut bone fit the prosthesis.

A. Precision Analysis

The precision analysis evaluated a cutting guide's ability to cut consistently in the same plane. After distal femoral condyle resection in a simulated total knee arthroplasty, the angle between the lateral and medial femoral condylar planes was measured. The precision of the cut was defined as the absolute value of the angular difference between the two condylar planes.

Methods for Experiment A1

Twelve 1145 urethane foam knees (Pacific Research Laboratories, Inc., Vashon, Wash.) were used. The rotating track cutting guide system and the Exodus® System were each tested with six knees and six new K-2000-25 3M Maxi-driver® blades (Komet Medical, Savannah, Ga.). After securing each cutting guide to a femur, the distal femoral condyles were resected. A Craftsman® Magnetic Universal Protractor (Sears, Hoffman Estates, Ill.) measured the angle of the lateral and medial condylar planes with respect to the ground. The protractor had an accuracy of ±0.5° and was maintained in a consistent orientation when placed on each condyle.

When measuring the condylar plane orientation, the angle indicated by the protractor was read by two individuals to account for user error. Both individuals separately measured the angles associated with the resected medial and lateral condylar planes. Each individual then calculated the angular difference between the two condylar planes and these values from the two individuals were compared. If the angular difference values differed, then the angles associated with the resected medial and lateral condylar planes were re-measured by each individual.

Methods for Experiment A2

The same procedure in Experiment A1 was performed, except that femora from twelve 1107-2 plastic-coated urethane foam knees were used. The 1107-2 urethane foam knees had a hard urethane elastomer cortex and were intended to model real bones more closely than the urethane foam bones.

Methods for Experiment A3

The same procedure in Experiment A1 was performed, except that the femora from fresh-frozen cadaver knees were used.

Analysis for the Precision Experiments

For the precision analysis, the absolute value of the angular difference between the two condylar planes was computed. For all the knees, a Fisher's Exact Test of Independence was used. This analysis is two-tailed test using a 2×2 table and compared the rate of existence of a zero difference between the Exodus® System and the rotating track cutting guide system. The experimental hypothesis was that the rotating track cutting guide system would have a higher rate of zero angular difference than the Exodus® System.

TABLE 1

Angular Difference (Degrees) Between the Condyles When Using the Exodus ® System and the Rotating Track Cutting Guide to Resect Foam Femora

| | Exodus ® System | Rotating Track Cutting Guide System |
|---|---|---|
| Bone 1 | 0 | 0 |
| Bone 2 | 0 | 0.5 |
| Bone 3 | 0 | 0 |
| Bone 4 | 0.5 | 0 |
| Bone 5 | 0 | 0 |
| Bone 6 | 0 | — |

TABLE 2

Angular Difference (Degrees) Between the Condyles When Using the Exodus ® System and Rotating Track Cuffing Guide to Resect Plastic-coated Femora

| | Exodus ® System | Rotating Track Cutting Guide System |
|---|---|---|
| Bone 1 | 0 | 0 |
| Bone 2 | 0.5 | 0 |
| Bone 3 | 0.5 | 0 |
| Bone 4 | 1 | 0 |
| Bone 5 | 0.5 | 0 |
| Bone 6 | 0.5 | 0 |

TABLE 3

Angular Difference (Degrees) Between the Condyles When Using the Exodus ® System and Rotating Track Cutting Guide to Resect Cadaver Femora

| | Exodus System | Rotating Track Cutting Guide |
|---|---|---|
| Bone 1 | 2.5 | 0 |
| Bone 2 | 1.5 | 0 |

TABLE 3-continued

Angular Difference (Degrees) Between the Condyles When Using the Exodus ® System and Rotating Track Cutting Guide to Resect Cadaver Femora

| | Exodus System | Rotating Track Cutting Guide |
|---|---|---|
| Bone 3 | 0 | 0.5 |
| Bone 4 | 0 | 0 |
| Bone 5 | 0.5 | 0 |
| Bone 6 | 0 | 0 |

Discussion

For the Precision Analysis using the foam femora and cadaver femora, no significant differences could be found between the performances of the two cutting systems. When the cadaver femora were resected, the largest indicator of the different levels of performance between the two cutting systems stemmed from the 2.5 degree angular difference between the resected medial condylar plane and the lateral condylar plane when using the Exodus® System. In our study, however, the sample size of six did not allow the results to be statistically significant. These results suggested that a larger sample size would be appropriate for a definitive statistical comparison.

The Fisher's Exact Test of Independence for plastic-coated bones indicated that the rotating track cutting guide system had a significantly higher rate of zero angular difference than the Exodus® System (P=0.015). The better performance of the rotating track cutting guide system in our study suggested that the rotating track cutting guide system cuts more precisely than the Exodus® System.

B. Blade Wear Analysis

The investigators made an examination of the blade wear associated with total knee arthroplasty. Reduced blade wear reflects the cutting guides' effectiveness for minimizing blade damage. Retained blade sharpness results in the more precise cutting of bone and a smoother bone surface.

Methods for Experiment B1

Two new K-2000-25 3M Maxi-driver® blades and 12 new 1145 urethane foam knees were obtained. One blade and six knees were randomly assigned to the cutting guides of the Exodus® System. The rotating track cutting guide system's cutting guides used the remaining blade and knees. The blades for the Exodus® and the rotating track cutting guide system's guides were weighed before their use. After performing all the femoral and tibial cuts in a simulated total knee arthroplasty, each blade was soaked overnight in acetone, dried and weighed. Repeated weighing of the blade ensured that a consistent blade weight value was obtained. A total of six simulated knee arthroplasties were performed using each blade and system, and the blade was weighed after each of the six procedures. The change in blade weight provided an indication of the average amount of blade wear associated with the use of each instrumentation system after one total knee arthroplasty.

Methods for Experiment B2

This experiment was similar to Experiment B1, but required the use of 12 new 1107-2 plastic-coated urethane foam knees. For additional qualitative information on blade damage, scanning electron microscopy provided 20×images of the blade teeth. SEM images of each blade were taken before the first arthroplasty and after the sixth procedure. Providing descriptive rather than quantitative information on blade damage, the images depicted the cumulated blade wear associated with each instrumentation system.

Analysis for the Blade Wear Experiments

The mean blade wear loss for each cutting system was calculated from six total knee arthroplasties. For the foam and plastic-coated knees, a repeated measures ANOVA compared the performance between the two cutting systems. The hypothesis was that the rotating track cutting guide system would result in less blade weight loss compared with the Exodus® System.

Results

TABLE 4

Blade Weight Loss Comparison Between the Exodus ® System and the Rotating Track Cutting Guide System After Performing Total Knee Arthroplasty on Six Foam Knees

|  | Exodus ® System | Rotating Track Cutting Guide System |
| --- | --- | --- |
| Trial 1 | 1.65 mg | 0.125 mg |
| Trial 2 | 1.2 mg | 0.125 mg |
| Trial 3 | 0.85 mg | 0.07 mg |
| Trial 4 | 2.5 mg | 0.03 mg |
| Trial 5 | 0.7 mg | 0.2 mg |
| Trial 6 | 1.6 mg | 0.0 mg |
| Total | 8.5 mg | 0.55 mg |
| Mean | 2.56 mg | 0.16 mg |

TABLE 5

Blade Weight Loss Comparison Between the Exodus ® System and the Rotating Track Cutting Guide System After Performing Total Knee Arthroplasty on Six Plastic-coated Knees.

|  | Exodus System | Rotating Track Cutting Guide System |
| --- | --- | --- |
| Trial 1 | −2.7 mg | 0.3 mg |
| Trial 2 | 9.8 mg | 1.55 mg |
| Trial 3 | 1.5 mg | 0 mg |
| Trial 4 | 0.7 mg | 0.2 mg |
| Trial 5 | 0.4 mg | 0 mg |
| Trial 6 | 1.25 mg | 0.1 mg |
| Total | 11 mg | 2.15 mg |
| Mean | 4.1 mg | 0.67 mg |

Blade damage was also qualitatively assessed by examining SEM images. The images with the Rotating track cutting guide system exhibited less cumulative blade damage than the Exodus® System.

Discussion

In the Blade Wear Analyses, a repeated measures ANOVA yielded a statistically significant difference in the blade wear between the rotating track cutting guide system and the Exodus® System (P=0.03). When resecting foam knees, there was often an order of magnitude difference in the blade weight loss between the rotating track cutting guide system and the Exodus® System. Use of the rotating track cutting guide system and the Exodus® System to resect plastic-coated knees showed a similar difference. There also existed a consistent wear pattern between each cutting system when resecting foam bones. The wear pattern, however, became less consistent when resecting plastic-coated bones. Additionally, the negative difference after the first blade wear trial for the Exodus® System was most likely due to plastic residue that remained on the blade after cleaning. Given the small sample size, more definitive conclusions can only be made after testing a larger number of blades.

The SEM images provided visual information that the rotating track cutting guide system was more effective in the retention of blade teeth sharpness than the Exodus® System. For the blade used by the rotating track cutting guide system, there was no deformation of the teeth closest to the sides of the saw blade, unlike with the blade used by the Exodus® System. The blade used by the rotating track cutting guide system, however, did have one row of blade teeth that was significantly worn. This wear pattern was probably due to the interference of the saw blade with the posterior cutting guide slots on the anterior and posterior femoral cutting guide subassembly. The experimental design of the rotating track cutting guide system did not include a method to attach and use the track subassembly to help guide the saw blade to resect the posterior femoral condyles. Consequently, the row of damaged teeth probably occurred from the saw blade not being oriented and stabilized with a track.

C. Femoral Component Fit Analysis

This experiment indicated the effectiveness of the cutting instrumentation through a fit assessment of the femoral component onto the femur. Although the use of PMMA allows a surgeon a greater margin of error when cutting bone, an uneven cement mantle can result in early prosthesis loosening. For this analysis, Ultra Low Pressurex® film (Sensor Products, Inc., East Hanover, N.J.) provided an image of the contact between the underside of the femoral component and the resected femoral surface. Decreased cutting effectiveness during resection would result in reduced contact area.

Methods for Experiment C1

In this experiment, 12 new plastic-coated femora and 12 new K-2000-25 3M blades were obtained. Six blades and femora were randomly selected and used with the Exodus cutting guides. The rotating track cutting guide system used the remaining blades and bones. Each system was used to perform the distal, anterior, posterior, anterior chamfer and posterior chamfer femoral cuts. The two halves of the Ultra Low Pressurex® film, the Transfer Sheet and the Developer Sheet, were individually cut into 3"×4.5" rectangles and folded to conform to the distal portion of the resected femur and to each other. After the Transfer Sheet and the Developer Sheet were gently placed upon one another to avoid inadvertent film activation, the femoral component was placed onto the distal femur. The high sensitivity Pressurex® film was used so that film activation would not depend solely on the impact force applied by the surgeon when placing the femoral component onto the bone. Contact between the underside of the femoral component and the resected femoral surface broke the chemical-filled microcapsules on the Transfer Sheet. This chemical reacted with the color developing material on the Developer Sheet and generated a residual red stain at the regions where the prosthesis and bone contacted. Unstained Pressurex® film indicated the location of the gaps between the implant and the cut bone.

Methods for Experiment C2

The same procedure as in experiment C1 was performed, except that fresh-frozen cadaver knees were used rather than plastic-coated knees.

Analysis

The contact area between the component and femur was calculated using SigmaScan® software. The data were normalized by dividing the contact area by the total area of the underside of the femoral component. After averaging the percent of contact data for the six femora with the two cutting systems, their means were compared. Plastic-coated knees required a two-sample t test for statistical analysis. The use of paired cadaver knees required a paired t-test for analysis. The hypothesis was that the rotating track cutting guide system would result in a higher percent of contact area than the Exodus® System

Results

Figure 20:
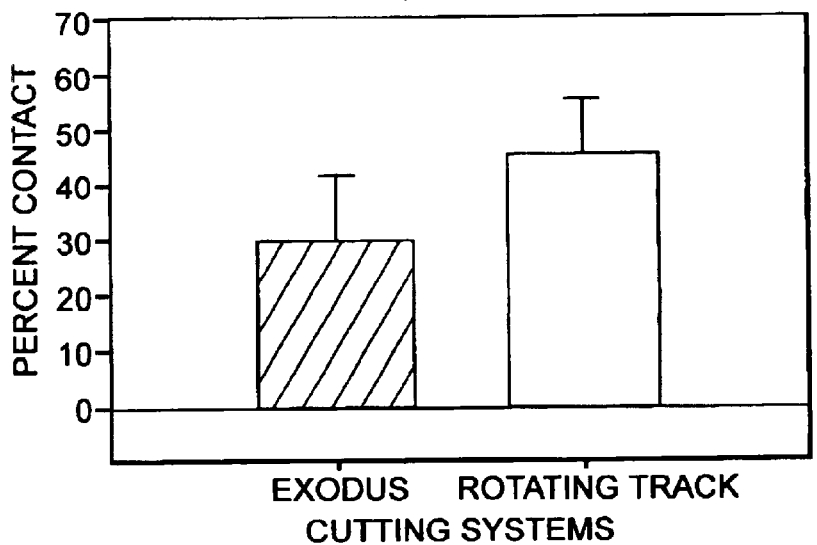
FIG. 20 is a graph summarizing experimental results for a precision comparison between the rotating track cutting guide and a prior art cutting system, each system cutting plastic-coated knees.
Figure 21:
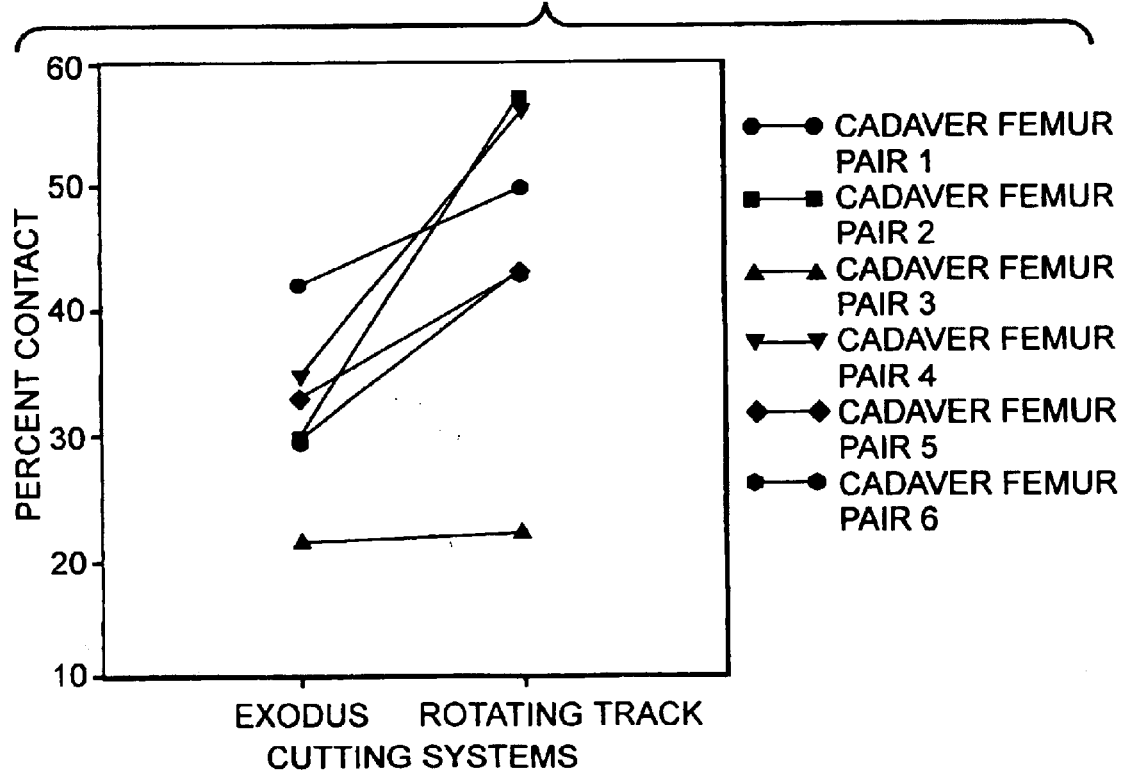
FIG. 21 is a graph summarizing experimental results for a precision comparison between the rotating track cutting guide and a prior art system, each system cutting cadaver knees.

Results of the femoral fit component fit analysis utilizing plastic coated femora and cadaver are summarized in graphs depicted as FIGS. 20 and 21 respectively.

Discussion

For the Femoral Component Fit Analysis using plastic-coated bones, use of the rotating track cutting guide system resulted in statistically significant increased contact between the underside of the femoral component and the resected femur than the Exodus® System (mean 42% vs. 28%, P=0.039). In the Femoral Component Fit Analysis with cadaver bones, use of the rotating track cutting guide system also resulted in statistically significant increased contact between the underside of the femoral component and the resected femur than the Exodus® System (mean 44% vs. 31%, P=0.021). Both results indicated that proper use of the rotating track cutting guide system resulted in greater contact between the resected bone surface and the prosthesis.

The distribution of contact percentages between each system may be attributed to how the cutting systems were designed and manufactured. For the Exodus® System, the cutting guide must be manually adjusted to the appropriate size before performing the chamfer cuts. A millimeter of difference can influence whether the femoral component will fit onto the resected bone surface. Consequently, half a millimeter of difference in the sizing of the cutting guide may have caused the contact percentage to range from 20–40%.

For the rotating track cutting guide system, one of the diagonal fixation holes of the medium chamfer cutting guide subassembly broke. This occurred as cadaver femur 3 was being resected. Consequently, the rotational motion of the medium chamfer cutting guide subassembly during the resecting process resulted in a low area contact percentage between the resected femoral surface and the prosthesis. The remaining variability in the performance of the rotating track cutting guide system was probably due to minor rotational motion of the large chamfer cutting guide subassembly during surgery.

D. Experiment Summary

The various analyses provided insight into the capabilities of the rotating track cutting guide system. The results of the Precision Analysis suggested that the rotating track cutting guide system resected the distal femur more precisely than a conventional cutting system. The Blade Wear Analysis proved a clearer suggestion that the rotating track cutting guide system produced statistically significant less blade wear on a saw blade than the Exodus® System. Use of the rotating track cutting guide system also resulted in statistical significant increased contact between the underside of the femoral component and the resected femur surface.

The present invention may be embodied in other specific forms without departing from the spirit of any of the essential attributes thereof; therefore, the illustrated embodiments should be considered in all respects as illustrative and not restrictive, reference being made to the appended claims rather than to the foregoing description to indicate the scope of the invention.

What is claimed is:

1. An orthopedic cutting guide system for precise planar cutting of bony tissue in association with orthopedic surgical procedures, the system comprising:

an alignment device adapted to support a surgical bone cutting saw driver, said saw driver driving a generally planar saw blade, said saw driver being supported by said alignment device such that movement of said blade is substantially fixed in a plane coplanar with the plane of said blade relative to said alignment device but the saw driver is free to move both translationally and rotationally relative to said alignment device, said alignment device further being oriented so that a long axis thereof extends generally outward and away from said bony tissue; and a cutting guide adapted to be removably attached to a bone and further adapted to releasably receive said alignment device in at least one nonajustable, substantially fixed position, said fixed position being precisely angularly oriented relative to said cutting guide and wherein said saw blade is passable throgh an aperture closely approximating a least dimension of said saw blade.

2. The orthopedic cutting guide system as claimed in claim 1, further comprising a carriage adapted to support said surgical bone cutting saw driver while allowing said saw blade driver to translate along and rotate relative to said alignment device.

3. The orthopedic cutting guide system as claimed in claim 1, in which said bone comprises a long bone having a longitudinal mechanical axis, said cutting guide comprising an attachment member adapted such that said alignment device is engaged to said bone such that said saw blade cuts a planar surface generally orthogonal to said longitudinal mechanical axis.

4. The orthopedic cutting guide system as claimed in claim 1, in which said bone comprises a long bone having a long axis, said cutting guide comprising an attachment member adapted such that said alignment device is engaged to said bone such that said saw blade cuts a planar surface generally oblique to said longitudinal mechanical axis.

5. The orthopedic cutting guide system as claimed in claim 1, in which said bone comprises a long bone having a longitudinal mechanical axis, cutting guide comprising an attachment member adapted such that said alignment device is aged to said bone engaged such that said saw blade cuts a planar surface generally parallel to said longitudinal mechanical axis.

6. The orthopedic cutting guide system as claimed in claim 1, in which said cutting guide is removably attached to said bone by a means selected from a consisting of clamps, screws, pins, adhesives and drill bits.

7. The orthopedic cutting guide system as claimed in claim 1, in which said alignment device is releasably secured to said cutting guide by at least one attachment member.

8. The orthopedic cutting guide system as claimed in claim 1, said cutting guide further defining alignment member receivers and said alignment device further comprising alignment members whereby said alignment device is precisely aligned with and releasably attached to said cutting guide.

9. The orthopedic cutting guide system as claimed in claim 1, which said aperture is defined by said cutting guide.

10. The orthopedic cutting guide system as claimed in claim 1, which said aperture is defined by said alignment device.

11. The orthopedic cutting guide system as claimed in claim 1, which said aperture is defined in part by said cutting guide and in part by said alignment device.

12. The orthopedic cutting guide system as claimed in claim 1, further comprising a selectively attachable femoral reference to aid locating said cutting guide.

13. The orthopedic cutting guide system as claimed in claim 1, in which said alignment device and said cutting guide are an integral unit.

14. The orthopedic cutting guide system as claimed in claim 2, in which said carriage movably engages with said alignment device via a mechanism selected from a group consisting of bushings, roller bearings, ball bearings and sliding bearings.

15. The orthopedic cutting guide system as claimed in claim 1, which said alignment device is releasably secured to said cutting guide via a mechanism selected from a group consisting of pegs, clips, screws, pins, bayonet fit and friction fit.

16. The orthopedic cutting guide system as claimed in claim 2, in which said carriage is secured to said surgical bone cutting saw driver by a means selected from a group consisting of screws, adhesives, clamping, pegs, clip, screws, pins, bayonet fit and a friction fit.

17. A method for precise planar cutting of bony tissue in association with orthopedic surgical procedures, the method comprising the steps of:

removably attaching a cutting guide to a bone;

removably securing an alignment device adapted to support a surgical bone cutting saw driver, said saw driver having a generally planar saw blade, said alignment device supporting said saw driver such that said blade is substantially fixed in a plane generally coplanar with the plane of said blade relative to said alignment device but the saw driver is free to move translationally and rotationally relative to said alignment device;

advancing said saw driver axially along said alignment device and manipulating said saw driver rotationally so as to cut said bone to create a desired first planar cut bone surface.

18. The method as claimed in claim 17, further comprising the step of relocating said cutting guide to a second location secured to said bone, said second location being chosen so as to allow the making of a second and additional planar surfaces precisely aligned relative to said first planar cut bone surface.

19. The method us claimed in claim 17, further comprising the step of utilizing a selectively attachable femoral reference to aid locating said cutting guide for creating said second and additional planar surfaces.

20. An orthopedic cutting guide system for precise planar cutting of bony tissue in association with orthopedic surgical procedures, the system comprising:

means for supporting a surgical saw driver having a generally planar saw blade such that said saw blade is substantially fixed in a pitch axis and a roll axis but the saw driver is free to move in a yaw axis and to translate axially relative to said supporting means;

means for guiding said saw blade, said guiding means adapted to be removably secured to a bone, said guiding means comprising means for removably, substantially rigidly receiving said supporting means whereby said surgical saw driver can be translated and yawed in order to prepare a precision cut substantially planar bone surface.

21. The orthopedic cutting guide system as claim in claim 20, further comprising a carriage adapted to support said surgical bone cutting sa driver while allowing said saw driver to translate along and rotate relative to said supporting means.

22. The orthopedic cutting guide system as claimed in claim 20, in which said bony tissue comprises a long bone having a longitudinal mechanical axis, said guiding means comprising an attachment member adapted inch that said supporting means is engaged to said bone such that said saw blade cuts a planar surface generally orthogonal to said longitudinal mechanical axis.

23. The orthopedic cutting guide system as claimed in claim 20, in which said bony tissue comprises a long bone having a longitudinal mechanical axis, said guiding means comprising an attachment member adapted such that said alignment device is engaged to said bone such that said saw blade cuts a planar surface generally oblique to said longitudinal mechanical axis.

24. The orthopedic cutting guide system as claimed in claim 20, in which said bony tissue comprises a long bone having a longitudinal mechanical axis, said guiding means comprising an attachment member adapted such that said alignment device is engaged to said bone engaged such that said saw blade cuts a planar surface gen eraly parallel to said long axis.

25. The orthopedic cutting guide system as claimed in clam 20, in which said guiding means is removably fixated to said bone by a means selected from a group consisting of clamps, screws, pins and drill bit.

26. The orthopedic cutting guide system s claimed in claim 20, in which said alignment device is releasably secured to said guiding means by at least one attachment member.

27. The orthopedic cutting guide system as claimed in claim 20, said guiding means further defining alignment member receivers and said alignment device further comprising alignment members whereby said alignment device is precisely aligned and releasably attached to said cutting guide.

28. The orthopedic cutting guide system as claimed in claim 20, in which an aperture closely approximating a least dimension of said saw blade is defined said guiding means.

29. The orthopedic cutting guide system as claimed in claim 20, in which an aperture closely approximating a least dimension of said saw blade is defined by said alignment device.

30. The orthopedic cutting guide system as claimed in claim 20, in which an aperture closely approximating a least dimension of said saw blade is defined part by said guiding means and in part by said alignment device.

31. The orthopedic cutting guide system as claimed in claim 20, further comprising a selectively attachable femoral reference to aid locating said guiding means.

32. The orthopedic cutting guide system as claimed in claim 20, further comprising a femoral reference to aid locating said guiding means.

33. An orthopedic cutting guide system for precise cutting of bony tissue in association with orthopedic surgical procedures, the system comprising:

a curved alignment device adapted to support a surgical bone cutting saw driver, said saw blade being supported such that movement of said saw driver is substantially fixed in parallel relationship relative to said alignment device but the saw driver is free to move translationally and rotationally relative to said alignment device, said alignment device further being oriented so that a path of travel of said saw driver along said alignment device extends generally across said bony tissue; and a cutting guide adapted to be removably fixated directly to a bone.

34. The orthopedic cutting guide system as claim in claim 33, further comprising a carriage adapted to support said surgical bone cutting saw driver while allowing said saw driver to move in a parallel fashion relative to said alignment device.

35. The orthopedic cutting guide system as claimed in claim 33, in which said cutting guide is removably fixated to said by bone a means selected from a group consisting of clamps, screws, pins, adhesives and drill bits.

36. The orthopedic cutting guide is system as claimed in claim 33, in which said aligment device is releasably secured to said cutting guide by at least one attachment member.

37. The orthopedic cutting guide system as claimed in claim 33, said cutting guide further defining alignment member receivers and said alignment device further comprising alignment members whereby said alignment device is precisely aligned and releasably attached to said cutting guide.

38. The orthopedic cutting guide system as claimed in claim 33, further comprising a selectively attachable femoral reference to aid locating said cutting guide.

39. The orthopedic cutting guide system as claimed in claim 33, in which said alignment device and said cutting guide are an integral unit.

40. The orthopedic cutting guide system as claimed in claim 33, in which said alignment device is releasably secured to said cutting guide via a mechanism selected from a group consisting of pegs, clips, screws, pins, bayonet fit and friction fit.

41. The orthopedic cutting guide system as claimed in claim 34, which said carriage movably engages with said alignment device via a mechanism selected from a group consisting of bushings, roller bearings, ball bearings and sliding bearings.

42. The orthopedic cutting guide system as claimed in claim 34, in which said carriage is secured to said surgical bone cutting saw driver by a means selected from a group consisting of screws, adhesives, clamping, pegs, clips, screws, pins, bayonet fit and friction fit.

43. An orthopedic cutting guide system for precise planar cutting of bony tissue in association with orthopedic surgical procedures, the system comprising:

an alignment device cutting guide comprising an alignment device portion and a cutting guide portion;

the alignment device portion adapted to support a surgical bone cutting saw driver, said saw driver having a generally planar saw blade, said saw driver being supported by said alignment device such that movement of said blade is substantially fixed in a plane coplanar with the plane of said blade relative to said alignment device portion but the saw driver is free to move translationally ad rotationally lative to said alignment device portion, said alignment device portion further being oriented so that a long axis thereof extends generally outward and away from said bony tissue; and the cutting guide portion adapted to be removably attached to a bone and further adapted to support said alignment device portion in a nonadjustable, substantially fixed position, said fixed position being precisely angularly oriented relative to said cutting guide and wherein said saw blade is passable through an aperture closely approximating a least dimension of said saw blade.

44. The orthopedic cutting guide system as claimed in claim 43, further comprising a carnage adapted to support said surgical bone cutting saw driver while allowing said saw driver to translate along and rotate relative to said alignment device portion.

45. The orthopedic cutting guide system as claimed in claim 43, in which said bone comprises a long bone having a longitudinal mechanical axis, said cutting guide comprising an attachment member adapted such that said alignment device portion is engaged to said bone such that said saw blade cuts a planar surface generally orthogonal to said longitudinal mechanical axis.

46. The orthopedic cutting guide system as claimed in claim 43, in which said bone comprises a long bone having a long axis, said cutting guide comprising an attachment member adapted such that said alignment device portion is engaged to said bone such that said saw blade cuts a planar surface generally oblique to said longitudinal mechanical axis.

47. The orthopedic cutting guide system as claimed in claim 43, in which said bone comprises a long bone having a longitudinal mechanical axis, said cutting guide comprising an attachment member adapted such that said alignment device portion is engaged to said bone engaged such that said saw blade cuts a planar surface generally parallel to said longitudinal mechanical axis.

48. The orthopedic cutting guide system as claimed in claim 43, in which said cutting guide portion is removably attached to said bone by a means selected from a group consisting of clamps, screws, pins, adhesives and drill bits.

49. The orthopedic cutting guide system as claimed in claim 43, which said alignment device portion is releasably secured to said cutting guide by at least means attachment member.

50. The orthopedic cutting guide system as claimed in claim 43, in which said aperture is defined by said cutting guide portion.

51. The orthopedic cutting guide system as claimed in claim 43, in which said aperture is defined by said alignment device portion.

52. The orthopedic cutting guide system as claimed in claim 43, in which said aperture is defined in part by said cutting guide and in part by said alignment device.

53. The orthopedic cutting guide system as claimed 43, further comprising a femoral reference to aid locating said cutting guide portion.

54. The orthopedic cutting guide system as claimed in claim 44, in which said carriage movably engages with said alignment device via a mechanism selected from a group consisting of bushings, roller bearings, ball bearings and sliding bearings.

55. The orthopedic cutting guide system as claimed in claim 43, in which said alignment device is releasably secured to said cutting guide via a mechanism selected from a group consisting of pegs, clip, screws, pins, bayonet fit and friction fit.

56. The orthopedic cutting guide system as claimed in claim 43, in which said carriage is secured to said surgical bone cutting saw driver by a means selected from a group consisting or screws, adhesives, clamping, pegs, clips, screws, pins, bayonet fit and a friction fit.

* * * * *

UNITED STATES PATENT AND TRADEMARK OFFICE
CERTIFICATE OF CORRECTION

PATENT NO.    : 6,858,032 B2
DATED         : February 22, 2005
INVENTOR(S)   : Chow et al.

It is certified that error appears in the above-identified patent and that said Letters Patent is hereby corrected as shown below:

Title page,
Item [75], Inventors, delete "Mendotah" and insert -- Mendota --.

Column 5,
Line 3, delete "chamber" and insert -- chamfer --.

Column 11,
Line 47, delete "Cuffing" and insert -- Cutting --.

Column 14,
Line 29, after "Exodus" insert -- ® --.

Column 16,
Line 13, delete "throgh" and insert -- through --.
Line 14, delete "a" and insert -- at --.
Line 36, after "axis," insert -- said --.
Line 38, delete "aged" and insert -- engaged --.
Line 43, before "consisting" insert -- group --.
Lines 55, 57 and 60, after "claim 1," insert -- in --.

Column 17,
Line 7, after "claim 1," insert -- in --.
Line 14, delete "clip" and insert -- clips --.
Line 38, delete "us" and insert -- as --.
Line 52, after "bone," insert -- and --.
Line 60, delete "sa" and insert -- saw --.
Line 66, delete "inch" and insert -- such --.

Column 18,
Line 15, delete "gen eraly" and insert -- generally --.
Line 19, delete "bit" and insert -- bits --.
Line 20, delete "s" and insert -- as --.
Lines 31, 34 and 38, delete "a" and insert -- at --.
Line 61, delete "claim" and insert -- claimed --.

UNITED STATES PATENT AND TRADEMARK OFFICE
CERTIFICATE OF CORRECTION

PATENT NO. : 6,858,032 B2
DATED : February 22, 2005
INVENTOR(S) : Chow et al.

It is certified that error appears in the above-identified patent and that said Letters Patent is hereby corrected as shown below:

Column 19,
Line 1, delete "by bone" and insert -- bone by --.
Line 3, delete "is".
Line 24, after "claim 34," insert -- in --.
Line 45, delete "lative" and insert -- relative --.
Line 56, delete "a" and insert -- at --.
Line 59, delete "carnage" and insert -- carriage --.

Signed and Sealed this

Twenty-sixth Day of July, 2005

JON W. DUDAS
*Director of the United States Patent and Trademark Office*